United States Patent [19]
Aida

[11] Patent Number: 6,090,540
[45] Date of Patent: Jul. 18, 2000

[54] METHODS FOR JUDGING THE POSSIBILITY OF THE ONSET OF BOVINE LEUKEMIA AND THE RESISTANCE THERETO

[75] Inventor: Yoko Aida, Ibaraki, Japan

[73] Assignee: The Institute of Physical and Chemical Research, Saitama, Japan

[21] Appl. No.: 09/147,550

[22] PCT Filed: Jul. 17, 1997

[86] PCT No.: PCT/JP97/02485

§ 371 Date: Apr. 23, 1999

§ 102(e) Date: Apr. 23, 1999

[87] PCT Pub. No.: WO98/03680

PCT Pub. Date: Jan. 29, 1998

[30] Foreign Application Priority Data

Jul. 19, 1996 [JP] Japan .................................. 8-190933
Mar. 28, 1997 [JP] Japan .................................. 9-077979

[51] Int. Cl.[7] .............................. C12Q 1/68; C12Q 1/70; C07H 21/04
[52] U.S. Cl. .................................. 435/5; 435/6; 435/91.2; 536/24.31; 536/24.33
[58] Field of Search .................................. 435/5, 6, 91.2; 536/24.33, 24.31

[56] References Cited

U.S. PATENT DOCUMENTS 5,567,809 10/1996 Apple et al. ............................ 536/24.3
5,582,987 12/1996 Lewin et al. ................................ 435/6

OTHER PUBLICATIONS

Armstrong et al., "Preferential site–dependent cleavage by restriction endonuclease Pst1", Nucleic Acid Research, vol. 10(3), pp. 993–1007, Dec. 1981.

Brooker, "Genetics: Analysis and Principles", p. 79, May 1999.

Aida et al. "Identification of a New Bovine MHC Class II DRB Allele by Nucleotide Sequencing and an Analysis of Phylogenetic Relationships", Biochemical and Biophysical Research Communications (1995) vol. 209, No. 3, pp. 981–988.

Stone et al. "Modulation of Bovine Leukemia Virus–Associated Spontaneous Lymphocyte Proliferation by Monoclonal Antibodies to Lymphocyte Surface Molecules", Clinical Immunology and Immunopathology (May 1997) vol. 83, No. 2, pp. 156–164.

Stone et al., "Up–regulation of IL–2 Receptor Alpha and MHC Class II Expression on Lymphocyte Subpopulation from Bovine Leukemia Virus Infected Lymphocytotic Cows", Veterinary Immunology and Immunopathology (1995) vol. 48, Nos. 1,2, pp. 65–76.

Hughes et al., "Proviruses of Avian Sacoma Virus Are Terminally Redundant, Co–Extensive with Unintegrated Linear DNA and Integrated at Many Sites", Cell, vol. 15, 1397–1410, Dec. 1978.

McKnight, "The Induction of Ovalbumin and Conalbumin mRNA by Estrogen and Progesterone in Chick Oviduct Explant Cultures" Cell, vol. 14, 403–413, Jun. 1978.

Miyaska et al., "Sheep as an Experimental Model for Immunology; Immunological Techniques in Vitro and in Vivo", Immunological Methods, vol. 3, pp. 403–423, 1985.

Levy et al., "Bovine Leukemia Virus Specific Antibodies Among French Cattle. I. Comparison of Complement Fixation and Hematological Tests", Int. J. Cancer, vol. 19, 822–827 (1977).

Aida et al., "Tumor–Associated $M_r$ and 34,000 and $M_r$ 32,000 Membrane Glycoproteins that are Serine Phosphorylated Specifically in Bovine Leukemia Virus–Induced Lymphosarcoma Cells", Cancer Research, vol. 52, 6463–6470, Dec. 1972.

*Primary Examiner*—Jeffrey Fredman
*Assistant Examiner*—Arun Chakrabarti
*Attorney, Agent, or Firm*—Greenblum & Bernstein, P.L.C.

[57] ABSTRACT

A method for judging a possibility of the onset of bovine leukemia caused by bovine leukemia virus BLV, wherein a bovine individual, in which an amino acid sequence defined by the amino acid numbers 75 to 78 of the β1 domain of the bovine MHC Class II DRβ chain is Val-Asp-Thr-Tyr, is judged to have a possibility of the onset of the leukemia: and a method for judging a resistance to the onset of bovine leukemia caused by the bovine leukemia virus BLV, wherein a bovine individual, in which an amino acid defined by the amino acid number 78 of the β1 domain of the bovine MHC Class II DRβ chain is Val, is judged to have a resistance to the onset of the leukemia.

8 Claims, 7 Drawing Sheets

```
SEQ ID NO:11  -29         5'UT              SP
SEQ ID NO:10    0             MetValCysLeuTyrPheSerGlyGlySerTrpMetAlaAlaIleValMetLeuValCysPro
                          CTCTGCTGTTCTCCGGCATGGTGTGCCTGTATTTCTCTGGAGGCTCCTGGATGGCAGCTCTGATAGTGATGCTGGTGTGCCCT
                                                        β1
   -5         ProLeuAlaTrpAlaArgGluIleGlnProHisPheLeuGluTyrThrLysGluCysHisPheAsnGlyThrGluArgValArg
   90         CCCCTGGCCTGGGCCAGGGAGATCCAACCACATTCCTGGAGTATACCAAGAAGAGTGTCATTTCTTCAACGGAACCGAGCGGGTGCGG

26         PheLeuAspArgTyrPheHisAsnGlyGluGluPheValArgPheAspSerAspTrpGlyGluTyrArgAlaValThrGluLeuGlyArg
   180        TTCCTGGACAGATACTTCCATAATGGAGAAGAGTTCGTGCGCTTCGACAGTGACTGGGGCGAGTACCGGGCGGTGACCGAGCTAGGGCGG

56         ProAspAlaLysTyrTrpAsnSerGlnLysAspPheLeuGluLeuLysArgAlaAlaValAspThrTyrCysArgHisAsnTyrGlyVal
   270        CCGGACGCCAAGTACTGGAACAGCCAGAAGGACTTCCTGGAGGAGAAGCGGGCCGCGGTGGACACGTACTGCAGACACAACTACGGGGTC
                                    β2
   86         GlyGluSerPheThrValGlnArgArgValGluProIleValThrValTyrProAlaLysThrGlnProLeuGlnHisHisAsnLeuLeu
   360        GGTGAGAGTTTCACTGTGCAGCGGCGAGTGGAACCTATAGTGACTGTGTATCCTGCAAAGACCCAGCCCCTGCAGCACCACAACCTCCTG

116        ValCysSerValAsnGlyPheTyrProGlyAsnIleGluValArgTrpPheArgAsnGlyHisGluGluAlaGlyValIleSerThr
   450        GTCTGCTCTGTGAACGGTTTCTACCCAGGCAACATTGAAGTCAGGTGGTTCCGAAATGGCCATGAAGAGGCTGGGGTGATCTCCACA
                                                               CP/TM/CY
   146        GlyLeuIleGlnAsnGlyAspTrpThrPheGlnThrMetValMetLeuGluThrValProGlnSerGlyGluValTyrThrCysGlnVal
   540        GGCCTGATCCAGAATGGAGACTGGACCTTCCAGACCATGGTGATGCTTGAAACAGTTCCTCAGAGTGGAGAGGTTACACCTGCCAAGTG

176        GluHisProSerGlnThrSerProIleThrValGluTrpArgAlaArgSerAspSerAlaGlnSerLysMetMetSerGlyValGlyGly
   630        GAGCACCCCAGCCAGACCAGCCCTATCACAGTAGAATGGAGGGCACGGTCTGACTCTGCTCAGAGCAAGATGATGAGTGGAGTCGGGGGC

206        PheValLeuGlyLeuPheLeuAlaValGlyLeuPheIleTyrPheArgAsnGlnLysGlyArgProThrLeuGlnProLeu
   720        TTCGTTCTGGGTCTGTTCCTTGCCGTGGGGCTCTTCATCTACTTCAGGAATCAGAAAGGACGCCCTACACTTCAGCCAACAGGGCTC
                                                                3'UT
   236        LeuSerEnd
   810        CTGAGCTGAAGTGAAGATGGTCACACTCAAGGAAGAACCTTCTGTCCCAGCTTCTTCACAGCATGGAAAGGTTCCTGCTTAGTGCTAAC

900        TCTTCCACAATGAAGTACTTTCTCAGGATCTCATTTGCTCCTGGCTCAGTGACCCCTTAAAAACTGTCTCCTGATGTTTTCTCAGTCACC
   990        TCCACCCTGCTGCCCTGCCCTCAGCCTTTGACCTGAAGTTCAATATTGATTCCAGTACCTTATGTTCTTCCTTGGTTCTTCCCTTCTTTT
  1080        CAACTTCTGTTTCCTGTGCATCGAGCTCATCTGTTCATTTTACTTTATAATGTGTTCTC
```

```
CATTLE WITH LYMPHOCYTOSIS
       9                                                                                86
       REIQPHFLEY TKKECHFFNG TERVRFLDRY FHNGEEFVRF DSDWGEYRAV TELGRPDAKY WNSQKDFLEE KRAAVDTYCR HNYGVG ESFTVQRR  SEQ ID NO:12
       .......... .......... .......... .......... .......... .......... .......... .......... ...... ........  SEQ ID NO:13
P1     ---------- ---------- ----N----- ---------- ---------- -----E---- ----EI--R- A--------- ------ --------  SEQ ID NO:14
       ---------- ---S------ ---------- -YT----N-- ---------- ------EQ-- ---------- --S R-T--- ---F-- --------  SEQ ID NO:15
       ---------- ---C-R---- ---------- -SY--K-R-- ------F--- ---S-E---- ---------- ----Q-R--- ---V-- --------  SEQ ID NO:16
P2     .......... .......... .......... .......... .......... .......... .......... .......... ...... ........  SEQ ID NO:17
       ---------- --Q- H-G--- ----L--H-- -----Y---- ---D-F---- ----S-E--- ---------- R R-E--V--- ------ --------
P3     .......... .......... .......... .......... .......... .......... .......... .......... ...... ........  SEQ ID NO:18
P4     ---------- ---------- -D---N---- ---------- ---------- -----E---- ----EI--R- A--------- ------ --------  SEQ ID NO:19
       ----------  --- STS---- -----Y---- ---------- ---------- --RV-EQ L-G- T--R E--Y-- ---------- ------ --------
P5     ---------- --- STS---S ----L----- ---------- -----F---- -----E---- ---------- --S R-T--- ------ ---I----  SEQ ID NO:20
       ---------- --- C-R---- ---------- ------C--- ---R-F---- -----A---- ---------- ---------- ------ --------  SEQ ID NO:21
P6     ---------- ---------- ----N----- ---------- --G------- ------E--- ----EI--R- A--------- ------ --------  SEQ ID NO:22
P7     ---------- ---S-S---- ---------- -----Y---- ---------- ----QRV-E- ----C----- R A-------- ---Y-- --------  SEQ ID NO:23
       ---------- ---S-S---- ---------- -YT----T-- ----F----- ------Q-EQ ---------- R A-------- ------ --------  SEQ ID NO:24
       ---------- --Q- H-G--- ----L--H-- -----Y---- ---D-F---- ----S-E--- ---------- R R-E--V--- ------ ---V----
```

ANTIBODY POSITIVE HEALTHY CATTLE NOT DEVELOPING LEUKEMIA

```
         9                                                                                      86
         REIQPHFLEY TKKECHFFNG TERVRFLDRY FHNGEEVRF DSDWGEYRAV TELGRPDAKY WNSQKDFLEE KRAAVDTYCR HNYGVG ESFTVQRR  SEQ ID NO:12
H1       ---------- --S-S----- ----E-S--- -------Y- ---------- -------E-- -------EI- --R-E--RV- ------ --------  SEQ ID NO:25
H2       ---------- --S-S----- ---------- --------- ---------- ---------- ---------- ---------- ------ --------  SEQ ID NO:26
H3       ---------- --S-S----- ----E-S--- ----Y---N --------- -------E-- -------EI-R --R-E--RV- ------ --------  SEQ ID NO:27
H4       ---------- --S-S----- ----E-S--- ----Y---N --------- ---------- -------EY- --R-E--RV- ------ --------  SEQ ID NO:28
H5       ---------- --------- ----N----- --------N --------- ---------- -------EI-R --R-E--RV- ------ --------  SEQ ID NO:29
H6       ---------- --C-R----- ---------- -------C- -------F- --RV-EQ--- -------EI-R A --R-E--RV- ------ --------  SEQ ID NO:30
H7       ---------- --------- ----N----- --------- --------- ---------- -------EI-- --R-E--RV- ---I-- --------  SEQ ID NO:31
H8       ---------- --C-S----- ----E-S--- ----Y---N --------- ---------- -------EI-R A --R-E--RV- ---V-- --------  SEQ ID NO:32
H9       ---------- --Q-H-G--- ----L--H-- ----Y---Y- ---D-F--- ---S-E---- -------EI-- --R-R-E--- ------ --------  SEQ ID NO:33
H10      ---------- --L-S----- ----E-S--- -------C- --------- --RV-EQ--- ---------L-R --R---N---- ---V-- --------  SEQ ID NO:34
H11      ---------- --C-R----- ---------- --------- ---D-F--- ---A-EQ--- -------EI-- ------Q--- ---V-- --------  SEQ ID NO:35
H12      ---------- --Q-H-G--L ----L--H-- ----Y---Y- ---D-F--- ---S-E---- -------EI-- --R-R-E--V ---V-- --------  SEQ ID NO:36
         ---------- --------- ---------- ----T---- --------- -------Q-E- -------EI-- --R-R-E--- ------ --------  SEQ ID NO:37
         ---------- --S-S----- ----E-S--- ----Y---N --------- -------E-- -------EI-R --R-E--RV- ------ --------  SEQ ID NO:38
         ---------- --------- ----N----- --------N --------- ---------- -------EI-R --R---N-RV- ------ --------  SEQ ID NO:39
         ---------- --S-S----- ---------- -------Y- --------- -------E-- -------EI-R --R-E--RV- ---GM- --------  SEQ ID NO:40
         ---------- --------- ---------- --------- --------- ---------- -------EI-R A --R-E--RV- ------ --------  SEQ ID NO:41
         ---------- --S-S----- ---------- ----Y---N --------- -------E-- -------EI-R --R-E--RV- ------ --------  SEQ ID NO:42
         ---------- --------- ----N----- --------- --------- -------E-- -------EI-R --R-E--RV- ------ --------  SEQ ID NO:43
         ---------- --------- ---------- --------- --------- -------E-- -------EI-R A ---S-R-T-- ------ --------  SEQ ID NO:44
         ---------- --S-S----- ---------- --YT--N-- ---F----- -------EQ- ---------- ---------- ------ -----F--  SEQ ID NO:45
```

FIG. 2B

ANTIBODY POSITIVE HEALTHY CATTLE NOT DEVELOPING LEUKEMIA

| | 9 | | | | | | | | | 86 | |
|---|---|---|---|---|---|---|---|---|---|---|---|
| | REIQPHFLEY | TKKECHFFNG | TERVRFLDRY | FHNGEEFVRF | DSDWGEYRAV | TELGRPDAKY | WNSQKDFLEE | KRAAVDTYCR | HNYGVG | ESFTVQRR | SEQ ID NO:12 |
| H13 | ---------- | -S-S------ | ---------- | ---S--Y--N- | ---------- | ------E--- | ---------I- | R-E--RV-- | ------ | -------- | SEQ ID NO:46 |
| H14 | ---------- | --STS----- | ---------- | ----Y----- | ---------- | -RV-EQ L-G--T-R | E--Y----- | ---------- | ------ | -------- | SEQ ID NO:47 |
| H15 | ---------- | -S-S------ | ---------- | ---YT----N- | ---F------ | ---EQ----- | ----------S | R-------- | ---F-- | -------- | SEQ ID NO:48 |
| H16 | ---------- | --ATS----- | ---------- | -----N---- | ---F------ | ---E------ | -----EI--R A---- | ---------- | ------ | -------- | SEQ ID NO:49 |
| H17 | ---------- | ---C-R---- | ---------- | -----Y---- | ---F------ | ---S-VP--- | ------G E--S---- | ---------- | ---V-- | -------- | SEQ ID NO:50 |
| H18 | ---------- | --Q--H-G-- | ---------- | ---L--H-Y--- | ---D-F---- | ---S-E---- | ---------- | R-E--RV-- | ------ | -------- | SEQ ID NO:51 |
| H19 | ---------- | --S-S----- | ---------- | ---E-S Y---N- | ---------- | ---S-E---- | ---------- | R R-E--V-- | ------ | -------- | SEQ ID NO:52 |
| H20 | ---------- | ---STS---- | ---------- | -----Y---- | ---D-F---- | -RV-EQ L-G---T-R | E--Y----- | ---------- | ---V-- | -------- | SEQ ID NO:53 |
| H21 | ---------- | --Q--H-G-- | ---------- | ---L--H-Y--- | ---D-F---- | ---A-EQ--- | --------Q- | ---E--RV-- | ---V-- | -------- | SEQ ID NO:54 |
| H22 | ---------- | ---------- | ---------- | -----N---- | ---------- | ----E----- | -----I--R A---- | ---------- | ---GV- | -------- | SEQ ID NO:55 |
| H23 | ---------- | --Q--H-G-- | ---------- | ---L--H-Y--- | ---D-F---- | ---S-E---- | ---------- | R R-E--V-- | ------ | -------- | SEQ ID NO:56 |
| H24 | ---------- | ---STS---- | ---------- | ---L------ | ---------- | ----E----- | -----.EI--R A---- | ---------- | ------ | -------- | SEQ ID NO:57 |
| | ---------- | ---------- | ---------- | ---YT----T- | ---F------ | ---Q-E---- | ---------- | ---E--RV-- | ---GM- | -------- | SEQ ID NO:58 |
| | ---------- | ---------- | ---------- | -----N---- | ---G------ | ---A-E---- | -----EI--R A---- | ---------- | ------ | -------- | SEQ ID NO:59 |
| | ---------- | ---H-G---- | ---------- | ---L--H-Y--- | ---D-F---- | ---S-E---- | ---------- | R R-E--V-- | ------ | -------- | SEQ ID NO:60 |
| | ---------- | ---STS---- | ---------- | ---------- | ---------- | ----E----- | -----.EI--R A---- | ---------- | ---GV- | -------- | SEQ ID NO:61 |
| | ---------- | ---Q--H-G- | ---------- | ---YT----T- | ---F------ | ---Q-E---- | -----EI--R A---- | ---------- | ---GM- | -------- | SEQ ID NO:62 |
| | ---------- | ---STS---- | ---------- | -----N---- | ---------- | ----E----- | -----EI--R A---- | ---------- | ------ | -------- | SEQ ID NO:63 |
| | ---------- | ---S-S---- | ---------- | ---------- | ---------- | QRV-E--C-- | ---------- | ---R A---- | ------ | -------- | SEQ ID NO:64 |
| | ---------- | ---------- | ---------- | ---------- | ---------- | ---------- | ---------- | ---------- | ------ | -------- | SEQ ID NO:65 |
| | ---------- | -S-S------ | ---------- | ---E-S Y---N- | ---------- | ----E----- | -----D--- | R-E--RV-- | ------ | -------- | SEQ ID NO:66 |

FIG. 2C

| CATTLE DEVELOPING LEUKEMIA | | | | | | | | | | |
|---|---|---|---|---|---|---|---|---|---|---|
| 9 | | | | | | | | 86 | | |
| REIQPHFLEY | TKKECHFFNG | TERVRFLDRY | FHNGEEFVRF | DSDWGEYRAV | TELGRPDAKY | WNSQKDFLEE | KRAAVDTYCR | HNYGVG | ESFTVQRR | SEQ ID NO:12 |
| L1 ......... | ---STS---- | ---------- | ---------- | ---------- | ---------- | ----.EI-R | A--------- | ------ | V------- | SEQ ID NO:67 |
| ......... | ---C-R---- | ---------- | ---------- | ---------- | ----A--Q-- | ---------- | ---------- | ------ | -V------ | SEQ ID NO:68 |
| L2 ......... | ---S-S---- | ---E-S---- | -Y----N--- | ---------- | ---RV-EQ-L | ---------Q | ------N--- | ------ | -------- | SEQ ID NO:69 |
| ......... | ---------- | ---------- | ---------- | ---------- | ---------R | ---------- | --------Q- | ------ | -------- | SEQ ID NO:70 |
| L3 ......... | .Q-H-G---- | -----L--H- | -Y----Y--- | ---D-F---- | ---------- | ---------- | --R-E--V-- | ------ | -V------ | SEQ ID NO:71 |
| L4 ......... | ---------- | -----N---- | ---------- | ---------- | ---------- | ------I--R | A--------- | ------ | -------- | SEQ ID NO:72 |
| ......... | ---S-S---- | ---------- | -Y-------- | ---------- | --QRV-E--C | ---------- | ------R A- | ------ | -------- | SEQ ID NO:73 |
| L5 ......... | ---S-S---- | ---------- | -Y-------- | ---------- | --QRV-E-S- | ---------- | ------R A- | ------ | -------- | SEQ ID NO:74 |
| ......... | ---S-S---- | ---------- | -Y-------- | ---------- | --QRV-E--C | ---------- | ------R A- | ------ | -------- | SEQ ID NO:75 |
| L6 ......... | ---------- | ---------- | ---------- | ---------- | ---------- | ---------- | ---------- | ------ | -------- | SEQ ID NO:76 |
| L7 ......... | ---S-S---- | ---------- | -YT---N--- | ---------- | ---------- | ----EQ---- | ------S R-T | ------ | F------- | SEQ ID NO:77 |
| ......... | ---S-S---- | ---E-S---- | -Y----N--- | ---F------ | ---------- | ----EI---R | ------E RV- | ------ | -------- | SEQ ID NO:78 |
| L8 ......... | ---STS---- | ---Y------ | ---------- | ---------- | ---RV-EQ L-G | ----T--R E-Y | ---------- | ------ | V------- | SEQ ID NO:79 |
| ......... | ---STS---- | ---Y------ | ---------- | ---D-F---- | ---RV-RQ L-G | ----T--R E-Y | ---------- | ------ | V------- | SEQ ID NO:80 |
| L9 ......... | .Q-H-G---L | -----L---- | -Y----Y--- | ---D-F---- | ----S-E--- | ---------- | --R-E--V-- | ------ | -V------ | SEQ ID NO:81 |
| ......... | ---H-G---- | -----L---- | -Y----Y--- | ---------- | ----S-E--- | ---------- | --R-E--V-- | ------ | -------- | SEQ ID NO:82 |
| L10 ........ | ---H-S-R-H | -----Y---- | -Y----Y--- | ---N-F---- | ---------- | ----E----- | ------R --- | ------ | I------- | SEQ ID NO:83 |
| ......... | ---S-S---- | ---------- | -YT---N--- | ---F------ | ---------- | ----EQ---- | ------S R-T | ------ | F------- | SEQ ID NO:84 |
| L11 ......... | ---S-S---- | ---------- | -Y----Y--- | ---F------ | ----A----- | ----E----- | ------I-R- | ------ | I------- | SEQ ID NO:85 |
| ......... | ---Y------ | ---------- | ---------- | ---F------ | ----A----- | ----Q--EQ- | ------R A- | ----Y- | -------- | SEQ ID NO:86 |
| L12 ........ | ---STR---- | ---------- | ---------- | ---------- | ---------- | ----E---H- | .EI-R A--- | ------ | --GV---- | SEQ ID NO:87 |
| ......... | ---Y-S---- | ---------- | -YT-G-T--- | ---F-L---- | ----Q--GQ- | ---------- | ------R A- | ----Y- | -------- | SEQ ID NO:88 |

CATTLE DEVELOPING LEUKEMIA

```
         9                                                                            86
     REIQPHFLEY TKKECHFFNG TERVRFLDRY FHNGEEFVRF DSDWGEYRAV TELGRPDAKY WNSQKDFLEE KRAAVDTYCR HNYGVG ESFTVQRR  SEQ ID NO:12
L13  ---------- ---------- ----L-E--- ----Y----- ---------- ----A----- ---------- ---S-R-T-- ------ --------  SEQ ID NO:89
     ---------- --S------- ---------- -YT----N-- ---------- -----EQ--- ---------- ---S-R-T-- ----F- --------  SEQ ID NO:90
L14  ---------- -STS---S-- ----L----- ---------- ---------- -----E---- ---------- ---S-R-T-- ----I- --------  SEQ ID NO:91
     ---------- -STS------ -------Y-- ---------- ---------- RV-EQ----- L-G--T-R-E-Y ---------- ------V --------  SEQ ID NO:92
L15  ---------- -S-S------ ---------- -YT----N-- ---------- -----E---- -----EI-R- ----R-A--- ------ --------  SEQ ID NO:93
     ---------- -Y-S------ ---------- -YT----T-- ---------- ---Q--EQ-- ---------- ----R-A--- ------I --------  SEQ ID NO:94
L16  ---------- -Y-S------ ---------- -YT----T-- ----F--L-- ---Q--EQ-- ---------- ----R-A--- ----Y- --------  SEQ ID NO:95
     ---------- -STS------ -------Y-- ---------- ----F----- RV-EQ----- L-G--T-R-E-Y ---------- ------V --------  SEQ ID NO:96
L17  ---------- -STS------ ---------- -YT----T-- ----F----- ---Q--E--- ---------- ----R-A--- ------ --------  SEQ ID NO:97
     ---------- -STS------ ---------- -YT----T-- ----F----- ---Q--E--- ---------- ----R-A--- ------ --------  SEQ ID NO:98
L18  ---------- -S-S------ ----E-S -Y- -----N---- ---------- RV-EQ----- L-----L--- -----E--RV ------V --------  SEQ ID NO:99
     ---------- ---------- ----L-E--- ----Y----- ---------- -----A---- ---------- -----N---- ------ --------  SEQ ID NO:100
L19  ---------- ---------- ---------- ---------- ---------- ---------- ---------- ---------- ------ --------  SEQ ID NO:101
     ---------- -S-S------ ---------- -YT----N-- ---------- -----EQ--- -----E---- ---S-R-T-- ----F- --------  SEQ ID NO:102
L20  ---------- ---------- ----N----- ---------- ---------- -----E---- -----EI-R- ----R-A--- ------ --------  SEQ ID NO:103
     ---------- -S-S------ ---------- -------Y-- ---------- QR-E--E--- -----E--C- ------R-A- ------ --------  SEQ ID NO:104
L21  ---------- ---------- ---------- ---------- ---------- ---------- -----E---- ------R-A- ------ --------  SEQ ID NO:105
     ---------- ---------- -------Y-- -------Y-- ----F--L-- RV-EQ----- L-G--T-R-E-Y ---------- ------V --------  SEQ ID NO:106
L22  ---------- -H-S------ ---------- -------Y-- ----F----- -----E---- -----EI-R- ---------- ------I --------  SEQ ID NO:107
     ---------- -Y-S------ ---------- -YT----T-- ---------- ---Q--EQ-- ---------- ----R-A--- ------ --------  SEQ ID NO:108
L23  ---------- -STS------ ---------- ---------- ---------- -----E---- -----.EI-R- ---S-R-T-- ---GV --------  SEQ ID NO:109
     ---------- -STS---S-- ----L----- ---------- ----F----- -----A---- -----E---- ----R-A--- ------I --------  SEQ ID NO:110
L24  ---------- -S-S------ ---------- ----Y----- ----D-F--- QRV-E----- -----S-E-- R-R-E--V-- ------V --------  SEQ ID NO:111
     ---------- -S-S------ ---------- ----Y----- ---------- ---------- ---------- ----R-A--- ------ --------
```

METHODS FOR JUDGING THE POSSIBILITY OF THE ONSET OF BOVINE LEUKEMIA AND THE RESISTANCE THERETO

This application is a 371 of PCT/JP97/02485 filed Jul. 17, 1997.

TECHNICAL FIELD

The present invention relates to a method for judging a possibility of the onset of bovine leukemia caused by bovine leukemia virus BLV and a resistance to the onset of the leukemia.

BACKGROUND ART

The major histocompatibility antigens (MHC antigens) are molecules involved in self-nonself differentiation in the defense mechanism of the living body against infection. They are classified into Class I molecule composed of α chain and β2M, and class II molecule composed of α chain and β chain. A groove for trapping an antigen peptide is present on the α1 and α2 domains, and also on the α1 and β1 domains. They are featured to have the T cell receptor recognize only a fragmented peptide trapped in the groove, thereby achieve cell death (cellular immunity) by CD8+ cells which have recognized the class I antigens, as well as induce mainly antibody production (humoral immunity) by CD4+ cells which have recognized the class 11 II antigens.

The MHC genes constitute a gene group most full of polymorphism, and the locations of pockets. shapes. sizes and properties of the peptide trapping grooves are different among haplotypes. It is considered that association conditicions of the trapped fragment peptides may vary depending on these differences, whict decide immune response and disease sensitivity of each individual. The correlation between the MHC haplotypes and a resistance to a disease (disease insusceptibility) or a possibility of the onset of a disease (disease susceptibility) has been reported, for example, as to human immune deficiency virus (HIV), human T cell leukemia virus (HTLV) and malaria.

As for the bovine MHC (BoLA) class II genes. existence of DQA, DQB, DRA, DRB, DNA, DOB, DYA, and DYB genes has been estimated. DRB3, inter atia. which is one of the three genes (DRB1 to B3) identified on the DRB genetic locus, has been known to encode a functional protein, and existence of 73 alleles has been revealed so far. However, there is almost no report about correlation between bovine infectious diseases and the bovine MHC (BoLA) haplotypes.

In particular, as to the bovine leukemia virus (BLV), which has the gene PX that regulates virus proliferation in the same manner as the human immunodeficiency virus (HIV) and is a retrovirus most related to HTLV-I, a research group in the United States has reported its relationship with the bovine MHC (BoLA) haplotypes mainly focusing disease resistance; however, its relationship with possibility of onset of the leukemia has not been reported. The ratio of cattle infected by this virus (infection rate in Japan) is 10–20%, and 1–2% of the infected cattle develops extremely malignant endemic bovine leukemia to die after a long latent period of 10–15 years. Therefore, economic loss of stockbreeders caused by the virus is very serious. If a possibility of the onset of a cattle after BLV infection can be evaluated by the analysis of bovine MHC (BoLA) haplotypes, it becomes possible to preliminarily select disease resistant cattle for bleeding, and it is expected that extremely safe cattle breeding can be continued.

Accordingly, an object of the present invention is to elucidate the relationship between the bovine leukemia virus (BLV) and the bovine MHC (BoLA) haplotypes, and to provide a method for convenient judgement of a possibility of the onset of leukemia of a cattle caused by the bovine leukemia virus (BLV) and a resistance to the onset of the leukemia by means of genetic engineering techniques. Another object of the present invention is to provide a primer set useful for the aforementioned method for judgement.

DISCLOSURE OF THE INVENTION

The inventors of the present invention previously analyzed the structure of DRB gene locus among the bovine MHC (BoLA) class II genes, and reported the structures of DRB3 gene (BoLA-DRB3) and the gene product thereof (Biochem. Biophys. Res. Commun., 209, pp.981–988, 1995). The inventors fiirther studied the function of the gene and found that a portion is present, whose amino acid sequence is distinctly different between a cattle developing the leukemia and a cattle not developing the disease, in the gene product from the second exon (β1 domain) of BoLA-DRB3 showing particularly noticeable polymorphism. They also found that the amino acid substitutions directly correlated with disease susceptibility to BLV and disease resistance. The present invention was achieved on the basis of these findings.

The present invention thus provides a method for judging a possibility of the onset of bovine leukemia caused by bovine leukemia virus BLV, wherein a bovine individual, in which an amino acid sequence defined by the amino acid number from 75 to 78 of the β1 domain of the bovine MHC Class II DRβ chain is Val-Asp-Thr-Tyr (SEQ ID NO: 9), is judged to have a possibility of the onset of the leukemia. As preferred embodiments of the method of the present invention, there are provided the aforementioned method which is applied to a cattle infected by the bovine leukemia virus BLV; and the aforementioned method wherein a bovine individual, in which an amino acid sequence defined by the amino acid numbers 75–78 of the β1 domain of the bovine MHC Class II DRβ chain is Val-Asp-Thr-Tyr (SEQ ID NO: 9) in both of the alleles, is judged to have a risk of the onset.

According to another embodiment of the method of the present invention, there is provided a method for judging a possibility of the onset of bovine leukemia caused by the bovine leukemia virus BLV, which comprises the steps of:

(1) amplifying genomic DNA isolated from a bovine individual by the polymerase chain reaction (PCR) to prepare a PCR product containing a DNA coding for a part or full length of the β1 domain of the bovine MHC Class II DRβ chain, and (2) judging that the bovine individual, in which an amino acid sequence corresponding to the amino acid number from 75 to 78 of the β1 domain of the bovine MHC Class II DRβ chain is Val-Asp-Thr (SEQ ID NO: 9) in the amino acid sequence encoded by the DNA contained in the PCR product, has a possibility of the onset of the leukemia. A preferred embodiment of the aforementioned method comprises a step of digesting the PCR product by using PstI.

According to another aspect of the present invention, there is provided a method for judging a resistance to the onset of bovine leukemia caused by the bovine leukemia virus BLV, wherein a bovine individual, in which an amino acid defined by the amino acid number 78 of the β1 domain of the bovine MHC Class II DRβ chain is Val, is judged to have resistant to the onset of the leukemia. As preferred embodiments of the method of the present invention, there are provided the aforementioned method which is applied to a cattle infected by the bovine leukemia virus BLV; the aforementioned method wherein the bovine individual, in which the amino acid specified by the amino acid number 78 of the β1 domain of the bovine MHC Class II DRβ chain is Val in at least one of the alleles, is judged to have a resistance to the onset; and the aforementioned method wherein the bovine individual, in which the amino acid specified by the amino acid number 78 of the β1 domain of the bovine MHC Class II DRβ chain is Val in both of the alleles, is judged to have a high resistance to the onset.

According to another embodiment of the method of the present invention, there is provided a method for judging a resistance to the onset of bovine leukemia caused by the bovine leukemia virus BLV, which comprises the steps of:

(1) amplifying genome DNA isolated from a bovine individual by the polymerase chain reaction (PCR) to prepare a PCR product containing a DNA coding for a part or full length of the β1 domain of the bovine MHC Class II DRβ chain, and (2) judging that the bovine individual, in which an amino acid corresponding to amino acid number 78 of the β1 domain of the bovine MHC Class II DRβ chain is Val in the amino acid sequence encoded by the DNA contained in the PCR product, has a resistance to the onset of the leukemia. A preferred embodiment of the aforementioned method comprises a step of digesting the PCR product by using PstI.

According to preferred embodiments of these inventions, there are provided each of the primer sets set out below, and the aforementioned methods wherein said primer set is used. preferably in those applied to cattle infected by the bovine leukemia virus BLV. Tle present invention further provides the following primer sets (1) to (3) each consisting of A primer and B primer, which are used for judging a possibility of the onset of bovine leukemia caused by the bovine leukemia virus BLV:

Primer set (1)

A primer: 5'-TGTAAAACGACGGCCAGTCTC TCTCTGCAGCACATTTCCT-3'(SEQ ID NO: 1)

B primer: 5'-CAGGAAACAGCTATGACCCGC CGCTGCACAGTGAAACTC-3'(SEQ ID NO: 2)

Primer set (2)

A primer: 5'-GGAATTCCTCTCTCTGCAGCA CATTTCCT-3'(SEQ ID NO: 3)

B primer: 5'-AAGTCGACCGCTGCACAGTGA AACTC-3'(SEQ ID NO: 4)

Primer set (3)

A primer: a primer which is selected from the group consisting of
5'-GAGTGTCATTTCTTCAACGGGAC-3'(SEQ ID NO: 5)
5'-GGAGAAGAGTTCGTGCGCTTCGA-3'(SEQ ID NO: 6), and
5'-GGAATTCCTCTCTCTGCAGCACATTTCCT-3' (SEQ ID NO: 7)

B primer: 5'-AAGTCGACCGCTGCACAGTGAAACTC-3' (SEQ ID NO: 8).

BRIEF DESCRIPTION OF THE DRAWINGS

FIGS. 2(A) to (C) show the results of comparison of amino acids of the β1 domain of the bovine MHC Class II DRβ chain (amino acid sequences defined by the amino acid number from 9 to 86) derived from cattle infected by the bovine leukemia virus BLV but not developing the disease ((A): 7 cattle developing lymphocytosis, and (B) and (C): antibody positive 24 healthy cattle not developing the disease). The numbers at the left end are ID numbers of bovine individuals, and amino acids indicated as one letter symbols in the figure.

FIGS. 3 (A) and (B) show the results of comparison of amino acids of the β1 domain of the bovine MHC Class II DRβ chain (amino acid sequences defined by the amino acid number from 9 to 86) derived from cattle developing leukemia (24 cattle). The numbers at the left end are ID numbers of bovine individuals. and amino acids are indicated as one letter symbols in the figure.

BEST MODE FOR CARRYING OUT THE INVNTION

Figure 1A:
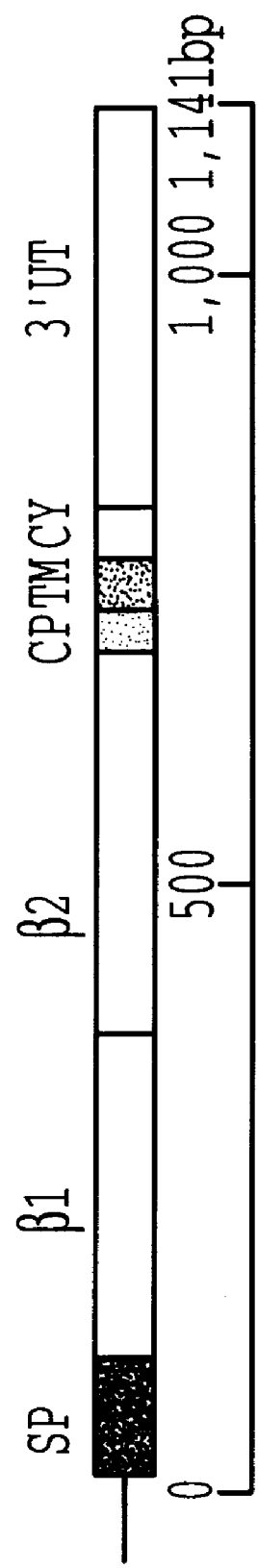
FIG. 1 depicts the structure of the bovine MHC Class II DRβ chain. In the figure, (A) shows the structure of bovine MHC Class II DRβ chain mRNA, and (B) shows the full length cDNA coding for the bovine MHC Class II DRβ chain and the amino acid sequence of the gene product. The β1 domain is a portion defined by the amino acid sequence of the amino acid number from 1 to 94.

The method of the present invention is applied to bovine individuals, including cattle infected with the bovine leukemia virus BLV and cattle not infected with the virus, in order to judge a possibility of the onset of the leukemia of the individuals. Another method of the present invention is applied to bovine individuals, including cattle infected with the bovine leukemia virus BLV and cattle not infected with the virus, in order to judge a resistance to the onset of the leukemia of the individuals.

According to a preferred embodiment of the present invention, genomic DNA of a bovine individual is isolated, and a gene coding for a part or the full length of the β1 domain of DRβ chain of the bovine MHC Class II (the second exon of DRB3 gene) is amplified by the PCR method, and then the resulting PCR product is subjected to a sequencing to deduce the amino acid sequence defined by the amino acid number from 75 to 78 of the β1 domain. When a bovine individual, in which the amino acid sequence (amino acid numbers 75 to 78) is Val-Asp-Thr-Tyr (SEQ ID NO: 9) (indicated as VDTY in the one letter symbols), is already with infection by the bovine leukemia virus BLV, or when the individual will suffer from infection by the bovine leukemia virus BLV, the bovine individual has a possibility of the onset of the leukemia. Whether or not a bovine individual is infected by the bovine leukemia virus BLV can be readily verified by a test using an antibody recognizing the bovine leukemia virus BLV.

In order to carry out more accurate judgement, it is preferred to compare the aforementioned amino acid sequences in the alleles (haplotypes). When the amino acid sequence (amino acid number 75 to 78) is Val-Asp-Thr-Tyr (SEQ ID NO: 9) in both of the alleles (i.e., VDTY homozygote), the bovine individual has a high risk of the onset of the leukemia when the individual is already infected by the bovine leukemia virus BLV, or will suffer from the infection by the virus. On the other hand, when the amino acid sequences in the alleles are heterozygote of Val-Asp-Thr-Tyr (SEQ ID NO: 9) (VDTY) and Val-Asp-Thr-Val (SEQ ID NO: 112) (VDTV); heterozygote of Val-Asp-Thr-Tyr (VDTY) (SEQ ID NO: 9) and Val-Asp-Arg-Val (VDRV) (SEQ ID NO: 113); homozygote of Val-Asp-Thr-Val (VDTV)(SEQ ID NO: 112); homozygote of Val-Aisp-Arg-Val (VDRV)(SEQ ID NO: 113); heterozygote of Val-Asp-Arg-Val(VDRV) (SEQ ID NO: 113) and Val-Asp-Thr-Val (VDTV) (SEQ ID NO: 112) or the like, the bovine individual has a very low possibility of the onset of the leukemia even if the bovine individual is already infected by the bovine leukemia virus BLV. or will suffer from the infection by the virus.

Furthermore, from a viewpoint of a resistance to the onset of he leukemia, the amino acid defined by the amino acid number 78 of the β1 domain may be deduced. When a bovine individual having Val (represented as V in the one letter symbol) as the amino acid (i.e., amino acid number 78) is already infected by the bovine leukemia virus BLV, or will suffer from infection by the virus, the bovine individual is resistant to the onset of the leukemia. Also for the judgement of the resistance, it is preferred to compare the aforementioned amino acid in the alleles (haplotypes). When the amino acid, defined by the amino acid number 78 of the β1 domain, is Val in at least one of the alleles, the individual has a resistance to the onset of the leukemia, and when the above amino acid is Val in both of the alleles, the individual has a high resistance to the onset of the leukemia.

The amino acid sequence of the β1 domain of the bovine MHC Class II DRβ chain was reported by Aida et al. (Aida, Y., et al., Biochem. Biophys. Res. Commun., 209, pp.981–988, 1995). The structure of mRNA of the bovine MHC Class II DRβ chain (A), and the full length cDNA and the amino acid sequence of the gene product (B) are shown in FIG. 1. In the figure, the β1 domain is a portion defined by the amino acid sequence of amino acid number from 1 to 94, and the nucleotide sequence and the amino acid sequence are shown where the peptide sequence of the amino acid number from 75 to 78 is "Val-Asp-Thr-Tyr (VDTY)". (SEQ ID NO: 9).

Cattle to be judged by the method according to the present invention are not particularly limited. The method may be applied to any sorts of cattle including dairy cattle, dairy and beef cattle, beef cattle, working cattle, working and beef cattle and the like, so long as they may be infected by the bovine leukemia virus BLV and have a possibility of developing the leukemia owing to the infection. More specifically, examples include Japanese cattle such as Japanese Black and Japanese Shorthorn, or breeds such as Holstein, Jersey, Hereford, Aberdeen Angus, and Friesian. However, breeds are not limited to these examples.

As a sample for preparing genomic DNA from bovine individuals, peripheral blood. organ and the like can be utilized. For example. a tissue section of the lymph node and other may be used as the organ. As methods for preparing genomic DNA from the sample mentioned above, any methods available to those skilled in the art can be employed. When peripheral blood leucocytes or peripheral blood lymphocytes are used as a sample, for example, the method of Hughes et al. (Hughes, S. H., Cell, 15, pp.1397–1410, 1978) may be applied. When an organ is used. for example, a frozen tissue section may be sliced by using scissors, and then treated by the sodium dodecylstilfate and phenol-chloroform method (Mcknight, G. S., Cell, 14, pp.403–413, 1978) to obtain genomic DNA. The simplified extraction of genomic DNA from cells may also be used, whose details are described in the examples.

As primers used for amplifying the resulting genomic DNA by the PCR method, any primers may be used so long as they can amplify a DNA containing a gene coding for a partial amino acid sequence of amino acid number from 75 to 78 of the β1 domain of the DRβ chain of the bovine MHC Class II or the full length of the β1 domain.

An example of a primer set most suitably used for the methods of the present invention includes primer set (1):

A primer: 5'-TGTAAAACGACGGCCAGTCTC TCTCTGCAGCACATTTCCT-3'(SEQ ID NO: 1); and

B primer: 5'-CAGGAAACAGCTATGACCCGC CGCTGCACAGTGAAACTC-3'(SEQ ID NO: 2)

which enables direct sequencing methods such as the cycle sequencing and the Dynabeads DNA direct sequencing. As primer sets introduced with a restriction endonuclease cleavage site, primer set (2):

A primer: 5'-GGAATTCCTCTCTCTGCAGCACATTTCCT-3' (SEQ ID NO: 3); and

B primer: 5'-AAGTCGACCGCTGCACAGTGAAACTC-3 (SEQ ID NO: 4), or primer set (3):

A primer: a primer selected from the group consisting of:

5'-GAGTGTCATTTCTTCAACGGGAC-3'(SEQ ID NO: 5),

5'-GGAGAAGAGTTCGTGCGCTTCGA-3'(SEQ ID NO: 6), and

5'-GGAATTCCTCTCTCTGCAGCACATTTCCT-3'(SEQ ID NO: 7); and

B primer: 5'-AAGTCGACCGCTGCACAGTGAAACTC-3' (SEQ ID NO: 8) may be utilized. In particular, by digesting PCR alleles with PstI that are amplified by using the primer set (3), and then observing differences in the resulting cleavage patterns, it can easily judge whether or not the bovine individual is resistant to the leukemia, or whether or not the individial has a possibility of the onset of the leukemia. However, primers and primer sets which may be used for the methods of the present invention are not limited to the forgoing examples.

An amount of DNA used for the PCR method can be appropriately chosen. For example, the amount may be about 0.1–0.5 µg when peripheral blood leucocytes or peripheral lymphocytes are used. As sequencing methods applied to the DNA amplified as descried above (the PCR product), any methods available to those skilled in the art may be utilized. For example, the direct sequencing may preferably be used, whose specific examples are described in the examples. Most of cattle are heterozygotes, and when alleles derived from father and mother cattle may have different nucleotide sequences, the direct sequencing may fail to determine which of the alleles corresponds to the target sequence. In that case, the PCR product amplified by using the above primer set (2) may be digested with restriction endonuclease EcoRI and Sal I, and then subcloned into a vector to carry out the sequencing of only one of the alleles, and the results may be referred to for comparison to enable a definite sequencing of the other allele. To obtain more precise genetic information, it is preferred that both of the alleles from the PCR product are subcloned and each of the nucleotide sequences is determined. The specific method and applicable primers are detailed in the following examples.

EXAMPLES

The present invention will be explained more specifically by referring to examples. However, the scope of the present invention is not limited to the examples set out below.

Example 1
Examination of a Possibility of the Onset of the Leukemia

Peripheral blood was collected as a sample from a bovine individual by using a syringe containing an anticoagulant, and centrifuged under conditions of 4° C. and 3,000 rpm for 20 minutes to obtain a leucocyte layer. The separated leucocyte layer was washed with phosphate buffered saline (PBS) and centrifuged to obtain a pellet, which washed as a sample of periipheral blood leucocyte. Peripheral blood lymphocytes were also obtained by the method of Miyasaka et al. (Miyasaka, M. and Trnka, Z., Immunological Methods, Vol.3, pp.403–423, 1985, Academic Press, NY) from peripheral blood obtained in the same manner as described above, and a sample of peripheral lymphocyte was prepared by obtaining a pellet as described above. A BLV infected cell suspension was centrifuged under conditions of 4° C. and 1,100 rpm for 5 minutes to remove a culture medium, and the cells were washed with PBS and centrifuged to obtain a pellet as a sample. In addition, tissue sections were isolated from the lymph node and a tumor tissue of a cattle which developed BLV infection lymphosarcoma, and rapidly frozen in liquid nitrogen without immobilization, and then stored at −80° C. as samples of the tissue sections.

Each of the above sample cells were washed twice with PBS in a 1.5 ml-microcentrifugal tube, and the precipitated cells were suspended again in PBS by using a vortex mixer. To 1×10$^6$ cells, 200 μl of 1×PCR buffer [10 mM Tris-HCl (pH 8.3), 50 mM KCl, 2.5 mM MgCl$_2$, 0.5% Tween-20] and 1 μl of Proteinase K (20 mg/ml) were added, and the cells were suspended again by a vortex mixer and incubated at 56° C. for 45–60 minutes. The mixture was further treated at 95° C. for ten minutes, and cooled on ice for 5 minutes or more. About 5–10 μl of the reaction mixture was used for amplification by PCR.

The genome DNA was dissolved in 50 μl of 1×PCR buffer [10 mM Tris-HCl (pH 8.3), 50 mM KCl, 1.5 mM MgCl$_2$, 0.001% (w/v) gelatin] containing 200 μM of each dNTP, 0.2–0.4 μM of primers, and 2.5 units of Taq polymerase (Gene Amp Kit; Perkin-Elmer Cetus), and then subjected to amplification by 25 cycles, each cycle consisting of treatments at 94° C. for 1 minute, at 61° C. for 1 minute, and at 72° C. for 1 minute, and then further treated at 72° C. for 5 minutes. As the primers, the following primers were used:

A primer: 5'-TGTAAAACGACGGCCAGTCTC TCTCTGCAGCACATTTCCT-3'(SEQ ID NO: 1)
B primer: 5'-CAGGAAACAGCTATGACCCGC CGCTGCACAGTGAAACTC-3'(SEQ ID NO: 2)

which can specifically amplify the β1 domain of the bovine MHC Class II DRβ chain (β1 domain of BoLA-DRβ: the second exon of DRB3 gene) by the PCR method. Specific biotinylation was introduced into the 5' end of the B primer. These primers can be suitably used for the cycle sequencing.

20 μl of DYNABEADS M-280 Streptoavidin (Dynal A. S, N-0212, Oslo, Norway) was washed with 100 μl of 2×binding-washing buffer (B&W buffer: 10 mM Tris-HCl (pH 7.5). 1.0 mM EDTA. 2M NaCl, 0.1% Tween-20), and the beads were suspended again in 80 μl of 2×B&W buffer. The above PCR product (50 μl ) was added to the bead suspension and gently mixed by pipetting, and then incubated at room temperature for 15 minutes with slow rotation using a wheel rotator. The tube containing the immobilized PCR product was put on a magnet (Dynal MPC) and the supernatant was removed by using a pipet, and then 100 μl of 2×B&W buffer was added to wash the beads. The supernatant was removed again by using a magnet, and the residue was suspended in 50 μl of 0.1 M NaOH prepared just before use.

The beads immobilizing the biotinylated chains were gathered on the tube wall by using a magnet and the supernatant was removed, and then the beads were washed once with 50 μl of 0.1 M NaOH and three times with 100 μl of 1×B&W buffer, and once with 50 μl of TE buffer. In every operation, the beads were resuspended with smooth strokes. After washing with 100 μl of distilled water, the supernatant was removed, and distilled water was added to the residue to adjust the volume for the use in a sequencing. The sequencing was performed by using BcaBEST Dideoxy Sequencing Kit (Takara Biomedicals) and according to the conditions described in the attached instructions. The following primers were used as sequencing primers.

Forward primer: 5'-TGTAAAACGACGGCCAGT-3'(SEQ ID NO: 114)
Reverse primer: 5'-CAGGAAACAGCTATGACC-3'(SEQ ID NO: 115)

The results are shown in FIGS. 2 and 3 (in the figures, amino acids of number 9 to 86 of the β1 domains of the bovine MHC Class II DRβ are shown, and the numbers at the left end are ID numbers of bovine individuals). By comparing the amino acids of the β1 domain of bovine MHC Class II DRβ derived from cattle infected by the bovine leukemia virus but not developing the leukemia [7 cattle with lymphocytosis (pre-cancer state), and 24 cattle not developing the leukemia (antibody positive healthy cattle not developing the disease), top and bottom of FIG. 2, respectively], and cattle already developing the leukemia (24 cattle, FIG. 3), a markedly characteristic result was obtained th at the cattle with the developed leukemia had Val-Asp-Thr-Tyr (VDTY) (SEQ ID NO: 9) motif as the sequence of amino acid number from 75 to 78 in both of the alleles. The portion of the amino acids from 75 to 78 is located on an α-helix of the β1 domain, and may have a function as a T cell recognition site. Furthermore, as a result of an analysis using a computer, it was revealed that this motif exists only in pol protein in the bovine leukemia virus BLV.

The above results are summarized in Table 1. The representation of the genotype such as VDTY/VDTY in the table indicates amino acid sequences of the both allele (amino acid number 75 to 78 of the μl domain of the bovine MHC Class II DRβ chain) described as the one letter symbols. The infection status of the BLV infected cattle were classified according to the criteria of Levy et al. (Levy, D., et al., Int. J. Cancer. 19, pp.822–827, 1977) and Aida et al. (Aida, Y., et al., Cancer Res., 52, pp.6463–6470, 1992).

TABLE 1

| | BLV infection status (positive rate) | | |
|---|---|---|---|
| Genotype | Development of leukemia | Lymphocytosis | Healthy |
| VDTY/VDTY | 19/24 | 5/7 | 4/24 |
| VDTY/VDTV | 2/24 | 2/7 | 2/24 |
| VDTY/VDRV | 2/24 | 0/7 | 14/24 |
| VDRV/VDRV | 0/24 | 0/7 | 1/24 |
| VDTV/VDTV | 1/24 | 0/7 | 0/24 |
| VDTV/VDRV | 0/24 | 0/7 | 3/24 |

Example 2
Study on Resistance to the Onset of Leukemia

It the same manner as in Example 1, kinds of the amino acid at number 78 of the β1 domains of bovine MHC Class II DRβ was determined for cattle developing the leukemia (24 cattle), cattle not developing the leukemia (cattle with lymphocytosis and healthy cattle, 31 individuals in total), and the results are shown in Table 2. The kind of the amino acids at numbers 71 and 74 were also determined (in the table, amino acids are indicated as one letter symbols, Y: Tyr; V: Val; R: Arg; E: Glu; K: Lys; and N: Asn). As a result, it was revealed that individuals where the 78th amino acid was heterozygote of valine and tyrosine, and individuals where the 78th amino acid was homozygote of valine were resistant to the onset of the leukemia, and in particular, the individuals where the 78th amino acid was homozygote of valine where lighly resistant to the onset of the leukemia. Furthermore, because all of the 74th amino acids of cattle not developing the leukemia were Gln or Asn, and the 71st amino acid residues were Lys or Arg, it was suggested that individuals having the allele where the 71st amino acid is lysine or arginine, the 74th amino acid is glutamic acid or asparagine, and the 78th amino acid is valine have high resistant to the onset of the leukemia.

TABLE 2

| Genotype | BLV infection status | Positive rate |
|---|---|---|
| $Y^{78}/Y^{78}$ | Cattle developing leukemia | 19/24 |
| $V^{78}/Y^{78}$ | Cattle developing leukemia | 4/24 |
| | $(R^{71}\text{-}E^{74}\text{-}V^{78}/Y^{78}$: | 3/24) |
| | $(K^{71}\text{-}E^{74}\text{-}V^{78}/Y^{78}$: | 1/24) |
| | $(K^{71}\text{-}N^{74}\text{-}V^{78}/Y^{78}$: | 0/24) |
| $V^{78}/V^{78}$ | Cattle developing leukemia | 1/24 |
| | $(R^{71}\text{-}E^{74}\text{-}V^{78}/R^{71}\text{-}E^{74}\text{-}V^{78}$: | 1/24) |
| | $(K^{71}\text{-}E^{74}\text{-}V^{78}/K^{71}\text{-}E^{74}\text{-}V^{78}$: | 0/24) |
| | $(K^{71}\text{-}N^{74}\text{-}V^{78}/K^{71}\text{-}N^{74}\text{-}V^{78}$: | 0/24) |
| $Y^{78}/Y^{78}$ | Cattle not developing leukemia | 9/31 |
| $V^{78}/Y^{78}$ | Cattle not developing leukemia | 18/31 |
| | $(R^{71}\text{-}E^{74}\text{-}V^{78}/Y^{78}$: | 11/31) |
| | $(K^{71}\text{-}E^{74}\text{-}V^{78}/Y^{78}$: | 4/31) |
| | $(K^{71}\text{-}N^{74}\text{-}V^{78}/Y^{78}$: | 3/31) |
| $V^{78}/V^{78}$ | Cattle not developing leukemia | 4/31 |
| | $(R^{71}\text{-}E^{74}\text{-}V^{78}/R^{71}\text{-}E^{74}\text{-}V^{78}$: | 3/31) |
| | $(K^{71}\text{-}E^{74}\text{-}V^{78}/K^{71}\text{-}E^{74}\text{-}V^{78}$: | 1/31) |
| | $(K^{71}\text{-}N^{74}\text{-}V^{78}/K^{71}\text{-}N^{74}\text{-}V^{78}$: | 0/31) |

Example 3
Method for Quick Judgement of Possibility and Resistance to the Onset

As described above, individuals having the gene coding for Val as the amino acid at number 78 of the β1 domain of the bovine MHC Class II DRβ chain are resistant to the leukemia caused by the bovine leukemia virus, whereas individuals where the 78th amino acid is Tyr in both of the alleles have a possibility of the onset of the leukemia. Therefore. whether or not an bovine individual is leukemia resistant, or whether or not an individual has a possibility of the onset of the leukemia is easily judged by utilizing restriction endonuclease PstI cleavage site which is present in a gene where the 78th allele is Val but absent in a gene where the 78th allele is Tyr, i.e., by digesting PCR amplified alleles and differentiating the cleavage pattern.

The following primers were used as PCR primers.

A primer

DRB40: 5'-GAGTGTCATTTCTTCAACGGGAC-3' (SEQ ID NO: 5)

DRB100: 5'-GGAGAAGAGTTCGTGCGCTTCGA-3' (SEQ ID NO: 6)

E R B 3 : 5'-GGAATTCCTCTCTCTGCAGCACATTTCCT-3' (SEQ ID NO: 7)

B primer

SRB3: 5'-AAGTCGACCGCTGCACAGTGAAACTC-3' (SEQ ID NO: 8).

The conditions of the PCR were similar to the conditions of Example 1. Specifically, amplification was performed by 35 cycles, each cycle consisting of the following steps depending on the combination of the primers, followed by a treatment at 72° C. for 10 minutes. The genomic DNA was used in an amount of 100 ng for 100 μl of the PCR system.

DRB40/SRB3: 94° C. for 1 minute, 63° C. for 2 minutes, 72° C. for 2 minutes

DRB100/SRB3: 94° C. for 1 minute, 66° C. for 2 minutes, 72° C. for 2 minutes

ERB3/SRB3: 94° C. for 1 minute, 61° C. for 2 minutes, 72° C. for 2 minutes

The PCR product was subjected to 2% agarose gel electrophoresis, and then cleaved by using restriction endonuclease PstI (1.2 μl of 10×restriction endonuclease buffer, 6–7 μl of DNA after amplification, 2 units of restriction endonuclease PstI, and H$_2$O in the total volume of 12 μl). After completion of the reaction with the restriction endonuclease, each specimen was examined by 3% agarose gel electrophoresis for judgement. The results are shown in Table 3.

TABLE 3

| Primer | PCR product (bp) | Size (bp) of PstI fragment | | | |
|---|---|---|---|---|---|
| | | Allele for Y | Allele for V | Y/Y | Y/V |
| DRB40/SRB3 | 247 | 199, 48 | 247 | 199, 48 | 247, 199, 48 |
| DRB100/SRB3 | 187 | 139, 48 | 187 | 139, 48 | 139, 187, 48 |
| ERB3/SRB3* | 292 | 226, 48 | 274 | 226, 48 | 226, 274, 48 |

*PstI cleavage site is present in the ERB3 primer, and hence a 18 bp fragment was contained in each reaction mixture.

INDUSTRIAL APPLICABILITY

A possibility of the onset of the leukemia caused by the bovine leukemia virus (BLV) and a resistance thereto of a bovine individual can be surely estimated by the methods of the present invention. Therefore, the invention enables safe cattle breeding and achieves prevention of economic loss of stockbreeders.

What is claimed is:

1. A method for judging a resistance to the onset of bovine leukemia caused by the bovine leukemia virus BLV, wherein a bovine individual, in whic an amino acid defined by the amino acid number 78 of the β1 domain of the bovine MHC Class II DR β chain is Val, is judged to have resistance to the onset of the leukemia.

2. The method according to claim 1, the bovine individual, in which the amino acid specified by the amino acid number 78 of the β1 domain of the bovine MHC Class II DRβ chain is Val in at least one of the alleles, is judged to have resistance to the onset.

3. The method according to claim 1 wherein the bovine individual, in which the amino acid specified by the amino acid number 78 of the β1 domain of the bovine MHC Class II DRβ chain is Val in both of the alleles, is judged to have high resistance to the onset.

4. A method for judging a resistance to the onset of bovine leukemia caused by bovine leukemia virus BLV, which comprises the steps of:

(1) amplifying genome DNA isolated from a bovine individual by the polymerase chain reaction to prepare a PCR product containing a DNA coding for a part or full length of the β1 domain of the bovine MHC Class II DRβ chain, and (2) judging that the bovine individual, in which an amino acid corresponding to the amino acid number 78 of the β1 domain of the bovine MHC Class II DRβ chain is Val in the amino acid sequence encoded by the DNA contained in the PCR product, has a resistance to the onset of the leukemia.

5. The method according to claim 4 which comprises a step of digesting the PCR product by using PstI.

6. A primer set used for judgement of a possibility of onset of bovine leukemia caused by bovine leukemia virus BLV or a resistance thereto, which comprises:

(a) A primer: 5'-TGTAAAACGACGGCCAGTCTC TCTCTGCAGCACATTTCCT-3'(SEQ ID NO: 1) and (b) B primer: 5'-CAGGAAACAGCTATGACCCGC CGCTGCACAGTGAAACTC-3'(SEQ ID NO: 2).

7. A primer set used for judgement of a possibility of onset of bovine leukemia caused by bovine leukemia virus BLV or a resistance thereto, which comprises:

(a) A primer: 5'-GGAATTCCTCTCTCTGCAGCA CATTTCCT-3'(SEQ ID NO: 3) and (b) B primer: 5'-AAGTCGACCGCTG (CACAGTGAAACTC-3'(SEQ ID NO: 4).

8. A primer set used for judgement of a possibility of onset of bovine leukemia caused by bovine leukemia virus BLV or a resistance thereto. which comprises:

(a) A primer which is selected from the group consisting of
   5'-GAGTGTCATTTCTTCAACGGGAC-3'(SEQ ID NO: 5)
   5'-GGAGAAGAGTTCGTGCGCTTCGA-3'(SEQ ID NO: 6), and
   5'-GGAATTCCTCTCTCTGCAGCACATTTCCT-3' (SEQ ID NO: 7), and (b) primer: 5'-AAGTCGACCGCTGCACAGTGA AACTC-3'(SEQ ID NO: 8).

* * * * *

UNITED STATES PATENT AND TRADEMARK OFFICE
CERTIFICATE OF CORRECTION

PATENT NO. : 6,090,540
DATED : July 18, 2000
INVENTOR(S) : Y. AIDA

It is certified that error appears in the above-identified patent and that said Letters Patent is hereby corrected as shown below:

At column 83, line 25 (claim 1, line 3) of the printed patent, "whic" should be ---which---.

At column 84, line 37 (claim 7, line 7) of the printed patent, delete " ( " (first occurrence).

At column 84, line 51 (claim 8, line 12) of the printed patent, after "(b)" insert ---B---.

Signed and Sealed this

Eighth Day of May, 2001

Attest:

NICHOLAS P. GODICI

*Attesting Officer*   *Acting Director of the United States Patent and Trademark Office*

SEQUENCE LISTING

<160> NUMBER OF SEQ ID NOS: 115

<210> SEQ ID NO 1
<211> LENGTH: 40
<212> TYPE: DNA

```
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 1
tgtaaaacga cggccagtct ctctctgcag cacatttcct                              40

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 2
caggaaacag ctatgacccg ccgctgcaca gtgaaactc                               39

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 3
ggaattcctc tctctgcagc acatttcct                                         29

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 4
aagtcgaccg ctgcacagtg aaactc                                            26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 5
gagtgtcatt tcttcaacgg gac                                               23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 6
ggagaagagt tcgtgcgctt cga                                               23

<210> SEQ ID NO 7
<211> LENGTH: 29
<212> TYPE: DNA
<213> ORGANISM: Artificial Sequence
```

```
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 7
ggaattcctc tctctgcagc acatttcct                                         29

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: PRIMER FOR
      JUDGING POSSIBILITY OF ONSET OF BOVINE LEUKEMIA

<400> SEQUENCE: 8
aagtcgaccg ctgcacagtg aaactc                                            26

<210> SEQ ID NO 9
<211> LENGTH: 4
<212> TYPE: PRT
<213> ORGANISM: BOVINE

<400> SEQUENCE: 9

Val Asp Thr Tyr
  1

<210> SEQ ID NO 10
<211> LENGTH: 1141
<212> TYPE: DNA
<213> ORGANISM: BOVINE

<400> SEQUENCE: 10
ctctgctgtt ctccggcatg gtgtgcctgt atttctctgg aggctcctgg atggcagctc         60
tgatagtgat gctgatggtg ctgtgccctc cctggcctg gccagggag atccaaccac         120 atttcctgga gtataccaag aaagagtgtc atttcttcaa cgggaccgag cgggtgcggt        180
tcctggacag atacttccat aatggagaag agttcgtgcg cttcgatagc gactggggcg        240
agtaccgggc ggtgaccgag ctagggcggc cggacgccaa gtactggaac agccagaagg        300
acttcctgga ggagaagcgg gccgcggtgg acacgtactg cagacacaac tacggggtcg        360
gtgagagttt cactgtgcag cggcgagtgg aacctatagt gactgtgtat cctgcaaaga        420
cccagcccct gcagcaccac aacctcctgg tctgctctgt gaacggtttc tacccaggca        480
acattgaagt caggtggttc cggaatggcc atgaagagga ggctggggtg atctccacag        540
gcctgatcca gaatggagac tggaccttcc agaccatggt gatgcttgaa acagttcctc        600
agagtggaga ggtctacacc tgccaagtgg agcacccccag ccagacaagc cctatcacag        660
tagaatggag ggcacggtct gactctgctc agagcaagat gatgagtgga gtcgggggct        720
tcgttctggg tctgttcttc cttgccgtgg ggctcttcat ctacttcagg aatcagaaag        780
gacgccctac acttcagcca acagggctcc tgagctgaag tgaagatggt cacactcaag        840
gaagaaccct ctgtcccagc ttcttcacag catggaaagg tttcctgctt agtgctaact        900
cttccacaat gaagtacttt tcaggatct catttgctcc tggctcagtg acccttaaa        960 aactgtcctc gatggttttc tcagtcacct ccaccctgct gccctcagcc tttgacctgg        1020
aagttctcaa tattgattcc agtaccttat gttcttttct ccttggttcc ctttctttc         1080 aacttctgtt tcctgtgcat ctgagctcat ctgttcattt tactttataa tgtgttctct        1140
c                                                                        1141
```

<210> SEQ ID NO 11
<211> LENGTH: 266
<212> TYPE: PRT
<213> ORGANISM: BOVINE

<400> SEQUENCE: 11

Met Val Cys Leu Tyr Phe Ser Gly Gly Ser Trp Met Ala Ala Leu Ile
 1               5                  10                  15

Val Met Leu Met Val Leu Cys Pro Pro Leu Ala Trp Ala Arg Glu Ile
             20                  25                  30

Gln Pro His Phe Leu Glu Tyr Thr Lys Lys Glu Cys His Phe Phe Asn
         35                  40                  45

Gly Thr Glu Arg Val Arg Phe Leu Asp Arg Tyr Phe His Asn Gly Glu
     50                  55                  60

Glu Phe Val Arg Phe Asp Ser Asp Trp Gly Glu Tyr Arg Ala Val Thr
 65                  70                  75                  80

Glu Leu Gly Arg Pro Asp Ala Lys Tyr Trp Asn Ser Gln Lys Asp Phe
                 85                  90                  95

Leu Glu Glu Lys Arg Ala Ala Val Asp Thr Tyr Cys Arg His Asn Tyr
            100                 105                 110

Gly Val Gly Glu Ser Phe Thr Val Gln Arg Arg Val Glu Pro Ile Val
        115                 120                 125

Thr Val Tyr Pro Ala Lys Thr Gln Pro Leu Gln His His Asn Leu Leu
    130                 135                 140

Val Cys Glu Val Asn Gly Phe Tyr Pro Gly Asn Ile Glu Val Arg Trp
145                 150                 155                 160

Phe Arg Asn Gly His Glu Glu Ala Gly Val Ile Ser Thr Gly Leu
                165                 170                 175

Ile Gln Asn Gly Asp Trp Thr Phe Gln Thr Met Val Met Leu Glu Thr
            180                 185                 190

Val Pro Gln Ser Gly Glu Val Tyr Thr Cys Gln Val Glu His Pro Ser
        195                 200                 205

Gln Thr Ser Pro Ile Thr Val Glu Trp Arg Ala Arg Ser Asp Ser Ala
    210                 215                 220

Gln Ser Lys Met Met Ser Gly Val Gly Gly Phe Val Leu Gly Leu Phe
225                 230                 235                 240

Phe Leu Ala Val Gly Leu Phe Ile Tyr Phe Arg Asn Gln Lys Gly Arg
                245                 250                 255

Pro Thr Leu Gln Pro Thr Gly Leu Leu Ser
            260                 265

<210> SEQ ID NO 12
<211> LENGTH: 94
<212> TYPE: PRT
<213> ORGANISM: BOVINE

<400> SEQUENCE: 12

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asp Arg Tyr Phe His
             20                  25                  30

Asn Gly Glu Glu Phe Val Arg Phe Asp Ser Asp Trp Gly Glu Tyr Arg
         35                  40                  45

Ala Val Thr Glu Leu Gly Arg Pro Asp Ala Lys Tyr Trp Asn Ser Gln
     50                  55                  60

```
Lys Asp Phe Leu Glu Glu Lys Arg Ala Ala Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 13
<211> LENGTH: 94
<212> TYPE: PRT
<213> ORGANISM: BOVINE

<400> SEQUENCE: 13

```
Arg Glu Ile Gln Pro His Phe Leu Glu Tyr Thr Lys Lys Glu Cys His
  1               5                  10                  15

Phe Phe Asn Gly Thr Glu Arg Val Arg Phe Leu Asn Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Pro Asp Ala Glu Tyr Trp Asn Ser Gln
 50                  55                  60

Lys Glu Ile Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 14
<211> LENGTH: 94
<212> TYPE: PRT
<213> ORGANISM: BOVINE

<400> SEQUENCE: 14

```
Arg Glu Ile Gln Pro His Phe Leu Glu Tyr Thr Lys Ser Glu Cys His
  1               5                  10                  15

Phe Phe Asn Gly Thr Glu Arg Val Arg Phe Leu Asp Arg Tyr Tyr Thr
                 20                  25                  30

Asn Gly Glu Glu Asn Val Arg Phe Asp Ser Asp Trp Gly Glu Phe Arg
             35                  40                  45

Ala Val Thr Glu Leu Gly Arg Pro Asp Ala Glu Gln Trp Asn Ser Gln
 50                  55                  60

Lys Asp Phe Leu Glu Ser Arg Arg Thr Ala Val Asp Thr Tyr Cys Arg
 65                  70                  75                  80

His Asn Tyr Gly Val Phe Glu Ser Phe Thr Val Gln Arg Arg
                 85                  90
```

<210> SEQ ID NO 15
<211> LENGTH: 94
<212> TYPE: PRT
<213> ORGANISM: BOVINE

<400> SEQUENCE: 15

```
Arg Glu Ile Gln Pro His Phe Leu Glu Tyr Cys Lys Arg Glu Cys His
  1               5                  10                  15

Phe Phe Asn Gly Thr Glu Arg Val Arg Phe Leu Asp Arg Tyr Ser Tyr
                 20                  25                  30

Asn Gly Lys Glu Arg Val Arg Phe Asp Ser Asp Trp Gly Glu Phe Arg
             35                  40                  45

Ala Val Thr Glu Leu Gly Arg Pro Ser Ala Glu Tyr Trp Asn Ser Gln
 50                  55                  60
```

```
Lys Asp Phe Leu Glu Gln Arg Arg Ala Ala Val Asp Thr Tyr Cys Arg
 65                  70                  75                  80

His Asn Tyr Gly Val Val Glu Ser Phe Thr Val Gln Arg Arg
                 85                  90
```

<210> SEQ ID NO 16
<211> LENGTH: 94
<212> TYPE: PRT
<213> ORGANISM: BOVINE

<400> SEQUENCE: 16

```
Arg Glu Ile Gln Pro His Phe Leu Gln Tyr His Lys Gly Glu Cys His
  1               5                  10                  15

Phe Phe Asn Gly Thr Glu Arg Val Arg Leu Leu Asp Arg His Phe Tyr
                 20                  25                  30

Asn Gly Glu Glu Tyr Val Arg Phe Asp Ser Asp Trp Asp Glu Phe Arg
             35                  40                  45

Ala Val Thr Glu Leu Gly Arg Pro Ser Ala Glu Tyr Trp Asn Ser Gln
         50                  55                  60

Lys Asp Phe Leu Glu Arg Arg Ala Glu Val Asp Thr Val Cys Arg
 65                  70                  75                  80

His Asn Tyr Gly Val Val Glu Ser Phe Thr Val Gln Arg Arg
                 85                  90
```

<210> SEQ ID NO 17
<211> LENGTH: 94
<212> TYPE: PRT
<213> ORGANISM: BOVINE

<400> SEQUENCE: 17

```
Arg Glu Ile Gln Pro His Phe Leu Glu Tyr Thr Lys Lys Glu Cys His
  1               5                  10                  15

Phe Phe Asn Gly Thr Asp Arg Val Arg Phe Leu Asn Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Pro Asp Ala Glu Tyr Trp Asn Ser Gln
         50                  55                  60

Lys Glu Ile Leu Glu Arg Ala Arg Ala Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 18
<211> LENGTH: 94
<212> TYPE: PRT
<213> ORGANISM: BOVINE

<400> SEQUENCE: 18

```
Arg Glu Ile Gln Pro His Phe Leu Glu Tyr Ser Thr Ser Glu Cys His
  1               5                  10                  15

Phe Phe Asn Gly Thr Glu Arg Val Arg Tyr Leu Asp Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Arg Val Ala Glu Gln Leu Asn Gly Gln
         50                  55                  60
```

```
Lys Asp Thr Leu Glu Arg Glu Arg Ala Tyr Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 19
<211> LENGTH: 94
<212> TYPE: PRT
<213> ORGANISM: BOVINE

<400> SEQUENCE: 19

```
Arg Glu Ile Gln Pro His Phe Leu Glu Tyr Ser Thr Ser Glu Cys His
 1               5                  10                  15

Phe Ser Asn Gly Thr Glu Arg Val Arg Leu Leu Asp Arg Tyr Phe His
                20                  25                  30

Asn Gly Glu Glu Phe Val Arg Phe Asp Ser Asp Trp Gly Glu Phe Arg
             35                  40                  45

Ala Val Ala Glu Leu Gly Arg Pro Asp Ala Glu Tyr Trp Asn Ser Gln
         50                  55                  60

Lys Asp Phe Leu Glu Ser Arg Thr Ala Val Asp Thr Tyr Cys Arg
 65                  70                  75                  80

His Asn Tyr Gly Val Ile Glu Ser Phe Thr Val Gln Arg Arg
                 85                  90
```

<210> SEQ ID NO 20
<211> LENGTH: 94
<212> TYPE: PRT
<213> ORGANISM: BOVINE

<400> SEQUENCE: 20

```
Arg Glu Ile Gln Pro His Phe Leu Glu Tyr Cys Lys Arg Glu Cys His
 1               5                  10                  15

Phe Phe Asn Gly Thr Glu Arg Val Arg Phe Leu Asp Arg Cys Phe His
                20                  25                  30

Asn Gly Glu Glu Phe Val Arg Phe Asp Ser Asp Arg Gly Glu Phe Arg
             35                  40                  45

Ala Val Thr Glu Leu Gly Arg Arg Val Ala Glu Gln Trp Asn Ser Gln
         50                  55                  60

Lys Asp Phe Leu Glu Glu Lys Arg Ala Ala Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 21
<211> LENGTH: 94
<212> TYPE: PRT
<213> ORGANISM: BOVINE

<400> SEQUENCE: 21

```
Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
                20                  25                  30

Asn Gly Glu Glu Phe Val Arg Phe Gly Ser Asp Trp Gly Glu Tyr Arg
             35                  40                  45

Ala Val Thr Glu Leu Gly Arg Pro Asp Ala Glu Tyr Trp Asn Ser Gln
         50                  55                  60

Lys Glu Ile Leu Glu Arg Ala Arg Ala Ala Val Asp Thr Tyr Cys Arg
```

-continued

```
                65                  70                  75                  80
His Asn Tyr Gly Val Gly Glu Ser Phe Thr Val Gln Arg Arg
                    85                  90

<210> SEQ ID NO 22
<211> LENGTH: 94
<212> TYPE: PRT
<213> ORGANISM: BOVINE

<400> SEQUENCE: 22

Arg Glu Ile Gln Pro His Phe Leu Glu Tyr Ser Lys Ser Glu Cys His
  1               5                  10                  15

Phe Phe Asn Gly Thr Glu Arg Val Arg Phe Leu Asp Arg Tyr Phe His
                 20                  25                  30

Asn Gly Glu Glu Tyr Val Arg Phe Asp Ser Asp Trp Gly Glu Tyr Arg
             35                  40                  45

Ala Val Thr Glu Leu Gly Gln Arg Val Ala Glu Tyr Cys Asn Ser Gln
         50                  55                  60

Lys Asp Phe Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                    85                  90

<210> SEQ ID NO 23
<211> LENGTH: 94
<212> TYPE: PRT
<213> ORGANISM: BOVINE

<400> SEQUENCE: 23

Arg Glu Ile Gln Pro His Phe Leu Glu Tyr Ser Lys Ser Glu Cys His
  1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Val Thr Glu Leu Gly Arg Gln Asp Ala Glu Gln Trp Asn Ser Gln
         50                  55                  60

Lys Asp Phe Leu Glu Arg Ala Arg Ala Ala Val Asp Thr Tyr Cys Arg
 65                  70                  75                  80

Tyr Asn Tyr Gly Val Gly Glu Ser Phe Thr Val Gln Arg Arg
                    85                  90

<210> SEQ ID NO 24
<211> LENGTH: 94
<212> TYPE: PRT
<213> ORGANISM: BOVINE

<400> SEQUENCE: 24

Arg Glu Ile Gln Pro His Phe Leu Gln Tyr His Lys Gly Glu Cys His
  1               5                  10                  15

Phe Phe Asn Gly Thr Glu Arg Val Arg Leu Leu Asp Arg His Phe Tyr
                 20                  25                  30

Asn Gly Glu Glu Tyr Val Arg Phe Asp Ser Asp Trp Asp Glu Phe Arg
             35                  40                  45

Ala Val Thr Glu Leu Gly Arg Pro Ser Ala Glu Tyr Trp Asn Ser Gln
         50                  55                  60

Lys Asp Phe Leu Glu Arg Arg Arg Ala Glu Val Asp Thr Val Cys Arg
 65                  70                  75                  80
```

His Asn Tyr Gly Val Val Glu Ser Phe Thr Val Gln Arg Arg
            85                  90

<210> SEQ ID NO 25
<211> LENGTH: 94
<212> TYPE: PRT
<213> ORGANISM: BOVINE

<400> SEQUENCE: 25

Arg Glu Ile Gln Pro His Phe Leu Glu Tyr Ser Lys Ser Glu Cys His
1               5                   10                  15

Phe Phe Asn Gly Thr Glu Arg Val Arg Phe Leu Glu Arg Ser Phe Tyr
            20                  25                  30

Asn Gly Glu Glu Tyr Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Glu Arg Arg Ala Glu Val Asp Arg Val Cys Arg
65                  70                  75                  80

His Asn Tyr Gly Val Gly Glu Ser Phe Thr Val Gln Arg Arg
            85                  90

<210> SEQ ID NO 26
<211> LENGTH: 94
<212> TYPE: PRT
<213> ORGANISM: BOVINE

<400> SEQUENCE: 26

Arg Glu Ile Gln Pro His Phe Leu Glu Tyr Ser Lys Ser Glu Cys His
1               5                   10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Lys Arg Ala Asn Val Asp Arg Val Cys Arg
65                  70                  75                  80

His Asn Tyr Gly Val Gly Glu Ser Phe Thr Val Gln Arg Arg
            85                  90

<210> SEQ ID NO 27
<211> LENGTH: 94
<212> TYPE: PRT
<213> ORGANISM: BOVINE

<400> SEQUENCE: 27

Arg Glu Ile Gln Pro His Phe Leu Glu Tyr Thr Lys Lys Glu Cys His
1               5                   10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Ala Arg Ala Ala Val Asp Thr Tyr Cys Arg
65                  70                  75                  80

His Asn Tyr Gly Val Gly Glu Ser Phe Thr Val Gln Arg Arg
            85                  90

<210> SEQ ID NO 28
<211> LENGTH: 94
<212> TYPE: PRT
<213> ORGANISM: BOVINE

<400> SEQUENCE: 28

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Tyr Leu Glu Glu Arg Arg Ala Glu Val Asp Arg Val Cys Arg
65                  70                  75                  80

His Asn Tyr Gly Val Gly Glu Ser Phe Thr Val Gln Arg Arg
            85                  90

<210> SEQ ID NO 29
<211> LENGTH: 94
<212> TYPE: PRT
<213> ORGANISM: BOVINE

<400> SEQUENCE: 29

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Lys Arg Ala Asn Val Asp Arg Val Cys Arg
65                  70                  75                  80

His Asn Tyr Gly Val Gly Glu Ser Phe Thr Val Gln Arg Arg
            85                  90

<210> SEQ ID NO 30
<211> LENGTH: 94
<212> TYPE: PRT
<213> ORGANISM: BOVINE

<400> SEQUENCE: 30

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Ala Arg Ala Ala Val Asp Thr Tyr Cys Arg
65                  70                  75                  80

His Asn Tyr Gly Val Ile Glu Ser Phe Thr Val Gln Arg Arg
            85                  90

<210> SEQ ID NO 31
<211> LENGTH: 94
<212> TYPE: PRT
<213> ORGANISM: BOVINE

<400> SEQUENCE: 31

Arg Glu Ile Gln Pro His Phe Leu Glu Tyr Cys Lys Arg Glu Cys His
 1               5                  10                  15

Phe Phe Asn Gly Thr Glu Arg Val Arg Phe Leu Asp Arg Cys Phe His
            20                  25                  30

Asn Gly Glu Glu Phe Val Arg Phe Asp Ser Asp Trp Gly Glu Phe Arg
        35                  40                  45

Ala Val Thr Glu Leu Gly Arg Arg Val Ala Glu Gln Trp Asn Ser Gln
    50                  55                  60

Lys Asp Phe Leu Glu Arg Arg Ala Glu Val Asp Arg Val Cys Arg
65                  70                  75                  80

His Asn Tyr Gly Val Val Glu Ser Phe Thr Val Gln Arg Arg
                85                  90

<210> SEQ ID NO 32
<211> LENGTH: 94
<212> TYPE: PRT
<213> ORGANISM: BOVINE

<400> SEQUENCE: 32

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Ala Arg Ala Ala Val Asp Thr Tyr Cys Arg
65                  70                  75                  80

His Asn Tyr Gly Val Gly Glu Ser Phe Thr Val Gln Arg Arg
                85                  90

<210> SEQ ID NO 33
<211> LENGTH: 94
<212> TYPE: PRT
<213> ORGANISM: BOVINE

<400> SEQUENCE: 33

Arg Glu Ile Gln Pro His Phe Leu Glu Tyr Cys Lys Ser Glu Cys His
 1               5                  10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Glu Arg Arg Ala Glu Val Asp Arg Val Cys Arg
65                  70                  75                  80

His Asn Tyr Gly Val Gly Glu Ser Phe Thr Val Gln Arg Arg
                85                  90

<210> SEQ ID NO 34
<211> LENGTH: 94
<212> TYPE: PRT
<213> ORGANISM: BOVINE

<400> SEQUENCE: 34

Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
             20                  25                  30

Asn Gly Glu Glu Tyr Val Arg Phe Asp Ser Asp Trp Asp Glu Phe Arg
         35                  40                  45

Ala Val Thr Glu Leu Gly Arg Pro Ser Ala Glu Tyr Trp Asn Ser Gln
     50                  55                  60

Lys Asp Phe Leu Glu Arg Arg Arg Ala Glu Val Asp Thr Val Cys Arg
 65                  70                  75                  80

His Asn Tyr Gly Val Val Glu Ser Phe Thr Val Gln Arg Arg
                 85                  90

<210> SEQ ID NO 35
<211> LENGTH: 94
<212> TYPE: PRT
<213> ORGANISM: BOVINE

<400> SEQUENCE: 35

Arg Glu Ile Gln Pro His Phe Leu Glu Tyr Leu Lys Ser Glu Cys His
 1               5                  10                  15

Phe Phe Asn Gly Thr Glu Arg Val Arg Phe Leu Glu Arg Ser Phe Tyr
             20                  25                  30

Asn Gly Glu Glu Asn Val Arg Phe Asp Ser Asp Trp Gly Glu Tyr Arg
         35                  40                  45

Ala Val Thr Glu Leu Gly Arg Pro Asp Ala Lys Tyr Trp Asn Ser Gln
     50                  55                  60

Lys Asp Leu Leu Glu Arg Lys Arg Ala Asn Val Asp Thr Tyr Cys Arg
 65                  70                  75                  80

His Asn Tyr Gly Val Val Glu Ser Phe Thr Val Gln Arg Arg
                 85                  90

<210> SEQ ID NO 36
<211> LENGTH: 94
<212> TYPE: PRT
<213> ORGANISM: BOVINE

<400> SEQUENCE: 36

Arg Glu Ile Gln Pro His Phe Leu Glu Tyr Cys Lys Arg Glu Cys His
 1               5                  10                  15

Phe Phe Asn Gly Thr Glu Arg Val Arg Phe Leu Asp Arg Cys Phe His
             20                  25                  30

Asn Gly Glu Glu Phe Val Arg Phe Asp Ser Asp Trp Gly Glu Phe Arg
         35                  40                  45

Ala Val Thr Glu Leu Gly Arg Arg Val Ala Glu Gln Trp Asn Ser Gln
     50                  55                  60

Lys Asp Phe Leu Glu Glu Arg Arg Ala Glu Val Asp Arg Val Cys Arg
 65                  70                  75                  80

His Asn Tyr Gly Val Val Glu Ser Phe Thr Val Gln Arg Arg
                 85                  90

<210> SEQ ID NO 37
<211> LENGTH: 94
<212> TYPE: PRT
<213> ORGANISM: BOVINE

<400> SEQUENCE: 37

Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
            20                  25                  30

Asn Gly Glu Glu Phe Val Arg Phe Asp Ser Asp Trp Asp Glu Phe Arg
        35                  40                  45

Ala Val Thr Glu Leu Gly Arg Pro Ala Ala Glu Gln Trp Asn Ser Gln
    50                  55                  60

Lys Asp Phe Leu Glu Gln Lys Arg Ala Glu Val Asp Arg Val Cys Arg
65                  70                  75                  80

His Asn Tyr Gly Val Gly Glu Ser Phe Thr Val Gln Arg Arg
                85                  90

<210> SEQ ID NO 38
<211> LENGTH: 94
<212> TYPE: PRT
<213> ORGANISM: BOVINE

<400> SEQUENCE: 38

Arg Glu Ile Gln Pro His Phe Leu Gln Tyr His Lys Gly Glu Cys His
 1               5                  10                  15

Phe Leu Asn Gly Thr Glu Arg Val Arg Leu Leu Asp Arg His Phe Tyr
            20                  25                  30

Asn Gly Glu Glu Tyr Val Arg Phe Asp Ser Asp Trp Asp Glu Phe Arg
        35                  40                  45

Ala Val Thr Glu Leu Gly Arg Pro Ser Ala Glu Tyr Trp Asn Ser Gln
    50                  55                  60

Lys Asp Phe Leu Glu Arg Arg Ala Glu Val Asp Thr Val Cys Arg
65                  70                  75                  80

His Asn Tyr Gly Val Gly Glu Ser Phe Thr Val Gln Arg Arg
                85                  90

<210> SEQ ID NO 39
<211> LENGTH: 94
<212> TYPE: PRT
<213> ORGANISM: BOVINE

<400> SEQUENCE: 39

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
            20                  25                  30

Asn Gly Glu Glu Thr Val Arg Phe Asp Ser Asp Trp Gly Glu Phe Arg
        35                  40                  45

Ala Val Thr Glu Leu Gly Arg Gln Asp Ala Glu Tyr Trp Asn Ser Gln
    50                  55                  60

Lys Asp Phe Leu Glu Glu Lys Arg Ala Glu Val Asp Arg Val Cys Arg
65                  70                  75                  80

His Asn Tyr Gly Gly Met Glu Ser Phe Thr Val Gln Arg Arg
                85                  90

-continued

<210> SEQ ID NO 40
<211> LENGTH: 94
<212> TYPE: PRT
<213> ORGANISM: BOVINE

<400> SEQUENCE: 40

Arg Glu Ile Gln Pro His Phe Leu Glu Tyr Ser Lys Ser Glu Cys His
1               5                   10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Lys Arg Ala Asn Val Asp Arg Val Cys Arg
65                  70                  75                  80

His Asn Tyr Gly Val Gly Glu Ser Phe Thr Val Gln Arg Arg
                85                  90

<210> SEQ ID NO 41
<211> LENGTH: 94
<212> TYPE: PRT
<213> ORGANISM: BOVINE

<400> SEQUENCE: 41

Arg Glu Ile Gln Pro His Phe Leu Glu Tyr Thr Lys Lys Glu Cys His
1               5                   10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Ala Arg Ala Ala Val Asp Thr Tyr Cys Arg
65                  70                  75                  80

His Asn Tyr Gly Val Gly Glu Ser Phe Thr Val Gln Arg Arg
                85                  90

<210> SEQ ID NO 42
<211> LENGTH: 94
<212> TYPE: PRT
<213> ORGANISM: BOVINE

<400> SEQUENCE: 42

Arg Glu Ile Gln Pro His Phe Leu Glu Tyr Ser Lys Ser Glu Cys His
1               5                   10                  15

Phe Phe Asn Gly Thr Glu Arg Val Arg Phe Leu Asp Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Glu Arg Arg Ala Glu Val Asp Arg Val Cys Arg
65                  70                  75                  80

His Asn Tyr Gly Val Gly Glu Ser Phe Thr Val Gln Arg Arg
                85                  90

<210> SEQ ID NO 43

```
<211> LENGTH: 94
<212> TYPE: PRT
<213> ORGANISM: BOVINE

<400> SEQUENCE: 43

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asp Arg Tyr Phe His
             20                  25                  30

Asn Gly Glu Glu Phe Val Arg Phe Asp Ser Asp Trp Gly Glu Tyr Arg
         35                  40                  45

Ala Val Thr Glu Leu Gly Arg Pro Asp Ala Glu Tyr Trp Asn Ser Gln
 50                  55                  60

Lys Glu Ile Leu Glu Arg Arg Ala Glu Val Asp Arg Val Cys Arg
 65                  70                  75                  80

His Asn Tyr Gly Val Gly Glu Ser Phe Thr Val Gln Arg Arg
                 85                  90

<210> SEQ ID NO 44
<211> LENGTH: 94
<212> TYPE: PRT
<213> ORGANISM: BOVINE

<400> SEQUENCE: 44

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
             20                  25                  30

Asn Gly Glu Glu Phe Val Arg Phe Asp Ser Asp Trp Gly Glu Tyr Arg
         35                  40                  45

Ala Val Thr Glu Leu Gly Arg Pro Asp Ala Glu Tyr Trp Asn Ser Gln
 50                  55                  60

Lys Glu Ile Leu Glu Arg Ala Arg Ala Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 45
<211> LENGTH: 94
<212> TYPE: PRT
<213> ORGANISM: BOVINE

<400> SEQUENCE: 45

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
             20                  25                  30

Asn Gly Glu Glu Asn Val Arg Phe Asp Ser Asp Trp Gly Glu Phe Arg
         35                  40                  45

Ala Val Thr Glu Leu Gly Arg Pro Asp Ala Glu Gln Trp Asn Ser Gln
 50                  55                  60

Lys Asp Phe Leu Glu Ser Arg Arg Thr Ala Val Asp Thr Tyr Cys Arg
 65                  70                  75                  80

His Asn Tyr Gly Val Phe Glu Ser Phe Thr Val Gln Arg Arg
                 85                  90

<210> SEQ ID NO 46
<211> LENGTH: 94
```

```
<212> TYPE: PRT
<213> ORGANISM: BOVINE

<400> SEQUENCE: 46

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Asp Ile Leu Glu Arg Arg Ala Glu Val Asp Arg Val Cys Arg
 65                  70                  75                  80

His Asn Tyr Gly Val Gly Glu Ser Phe Thr Val Gln Arg Arg
                85                  90

<210> SEQ ID NO 47
<211> LENGTH: 94
<212> TYPE: PRT
<213> ORGANISM: BOVINE

<400> SEQUENCE: 47

Arg Glu Ile Gln Pro His Phe Leu Glu Tyr Ser Thr Ser Glu Cys His
 1               5                  10                  15

Phe Phe Asn Gly Thr Glu Arg Val Arg Tyr Leu Asp Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Arg Val Ala Glu Gln Leu Asn Gly Gln
    50                  55                  60

Lys Asp Thr Leu Glu Arg Glu Arg Ala Tyr Val Asp Thr Tyr Cys Arg
 65                  70                  75                  80

His Asn Tyr Gly Val Val Glu Ser Phe Thr Val Gln Arg Arg
                85                  90

<210> SEQ ID NO 48
<211> LENGTH: 94
<212> TYPE: PRT
<213> ORGANISM: BOVINE

<400> SEQUENCE: 48

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
            20                  25                  30

Asn Gly Glu Glu Asn Val Arg Phe Asp Ser Asp Trp Gly Glu Phe Arg
        35                  40                  45

Ala Val Thr Glu Leu Gly Arg Pro Asp Ala Glu Gln Trp Asn Ser Gln
    50                  55                  60

Lys Asp Phe Leu Glu Ser Arg Arg Ala Ala Val Asp Thr Tyr Cys Arg
 65                  70                  75                  80

His Asn Tyr Gly Val Phe Glu Ser Phe Thr Val Gln Arg Arg
                85                  90

<210> SEQ ID NO 49
<211> LENGTH: 94
<212> TYPE: PRT
```

<213> ORGANISM: BOVINE

<400> SEQUENCE: 49

```
Arg Glu Ile Gln Pro His Phe Leu Glu Tyr Thr Lys Lys Glu Cys His
 1               5                  10                  15
Phe Phe Asn Gly Thr Glu Arg Val Arg Phe Leu Asn Arg Tyr Phe His
             20                  25                  30
Asn Gly Glu Glu Phe Val Arg Phe Asp Ser Asp Trp Gly Glu Tyr Arg
         35                  40                  45
Ala Val Thr Glu Leu Gly Arg Pro Asp Ala Glu Tyr Trp Asn Ser Gln
     50                  55                  60
Lys Glu Ile Leu Glu Arg Ala Arg Ala Val Asp Thr Tyr Cys Arg
 65                  70                  75                  80
His Asn Tyr Gly Val Gly Glu Ser Phe Thr Val Gln Arg Arg
                 85                  90
```

<210> SEQ ID NO 50
<211> LENGTH: 94
<212> TYPE: PRT
<213> ORGANISM: BOVINE

<400> SEQUENCE: 50

```
Arg Glu Ile Gln Pro His Phe Leu Glu Tyr Ala Thr Ser Glu Cys His
 1               5                  10                  15
Phe Phe Asn Gly Thr Glu Arg Val Arg Phe Leu Asp Arg Tyr Phe His
             20                  25                  30
Asn Gly Glu Glu Leu Val Arg Phe Asp Ser Asp Trp Gly Glu Phe Arg
         35                  40                  45
Ala Val Thr Glu Leu Gly Arg Pro Ser Ala Val Pro Trp Asn Ser Gln
     50                  55                  60
Lys Asp Phe Leu Glu Gly Glu Arg Ala Ser Val Asp Thr Tyr Cys Arg
 65                  70                  75                  80
His Asn Tyr Gly Val Val Glu Ser Phe Thr Val Gln Arg Arg
                 85                  90
```

<210> SEQ ID NO 51
<211> LENGTH: 94
<212> TYPE: PRT
<213> ORGANISM: BOVINE

<400> SEQUENCE: 51

```
Arg Glu Ile Gln Pro His Phe Leu Glu Tyr Cys Lys Arg Glu Cys His
 1               5                  10                  15
Phe Phe Asn Gly Thr Glu Arg Val Arg Phe Leu Asp Arg Tyr Phe Tyr
             20                  25                  30
Asn Gly Glu Glu Tyr Val Arg Phe Asp Ser Asp Trp Gly Glu Phe Arg
         35                  40                  45
Ala Val Thr Glu Leu Gly Arg Pro Asp Ala Glu Tyr Trp Asn Ser Gln
     50                  55                  60
Lys Asp Phe Leu Glu Arg Arg Ala Glu Val Asp Arg Val Cys Arg
 65                  70                  75                  80
His Asn Tyr Gly Val Gly Glu Ser Phe Thr Val Gln Arg Arg
                 85                  90
```

<210> SEQ ID NO 52
<211> LENGTH: 94
<212> TYPE: PRT
<213> ORGANISM: BOVINE

<400> SEQUENCE: 52

Arg Glu Ile Gln Pro His Phe Leu Gln Tyr His Lys Gly Glu Cys His
1               5                   10                  15

Phe Phe Asn Gly Thr Glu Arg Val Arg Leu Leu Asp Arg His Phe Tyr
            20                  25                  30

Asn Gly Glu Glu Tyr Val Arg Phe Asp Ser Asp Trp Asp Glu Phe Arg
        35                  40                  45

Ala Val Thr Glu Leu Gly Arg Pro Ser Ala Glu Tyr Trp Asn Ser Gln
    50                  55                  60

Lys Asp Phe Leu Glu Arg Arg Ala Glu Val Asp Thr Val Cys Arg
65                  70                  75                  80

His Asn Tyr Gly Val Val Glu Ser Phe Thr Val Gln Arg Arg
                85                  90

<210> SEQ ID NO 53
<211> LENGTH: 94
<212> TYPE: PRT
<213> ORGANISM: BOVINE

<400> SEQUENCE: 53

Arg Glu Ile Gln Pro His Phe Leu Glu Tyr Ser Lys Ser Glu Cys His
1               5                   10                  15

Phe Phe Asn Gly Thr Glu Arg Val Arg Phe Leu Glu Arg Ser Phe Tyr
            20                  25                  30

Asn Gly Glu Glu Asn Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Glu Ile Leu Glu Arg Arg Ala Glu Val Asp Arg Val Cys Arg
65                  70                  75                  80

His Asn Tyr Gly Val Gly Glu Ser Phe Thr Val Gln Arg Arg
                85                  90

<210> SEQ ID NO 54
<211> LENGTH: 94
<212> TYPE: PRT
<213> ORGANISM: BOVINE

<400> SEQUENCE: 54

Arg Glu Ile Gln Pro His Phe Leu Glu Tyr Ser Thr Ser Glu Cys His
1               5                   10                  15

Phe Phe Asn Gly Thr Glu Arg Val Arg Tyr Leu Asp Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Arg Val Ala Glu Gln Leu Asn Gly Gln
    50                  55                  60

Lys Asp Thr Leu Glu Arg Glu Arg Ala Tyr Val Asp Thr Tyr Cys Arg
65                  70                  75                  80

His Asn Tyr Gly Val Val Glu Ser Phe Thr Val Gln Arg Arg
                85                  90

<210> SEQ ID NO 55
<211> LENGTH: 94
<212> TYPE: PRT
<213> ORGANISM: BOVINE

<400> SEQUENCE: 55

Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
            20                  25                  30

Asn Gly Glu Glu Phe Val Arg Phe Asp Ser Asp Trp Asp Glu Phe Arg
        35                  40                  45

Ala Val Thr Glu Leu Gly Arg Pro Ala Ala Glu Gln Trp Asn Ser Gln
    50                  55                  60

Lys Asp Phe Leu Glu Gln Lys Arg Ala Glu Val Asp Arg Val Cys Arg
65                  70                  75                  80

His Asn Tyr Gly Gly Val Glu Ser Phe Thr Val Gln Arg Arg
                85                  90

<210> SEQ ID NO 56
<211> LENGTH: 94
<212> TYPE: PRT
<213> ORGANISM: BOVINE

<400> SEQUENCE: 56

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
        35                  40                  45

Ala Val Thr Glu Leu Gly Arg Pro Asp Ala Glu Tyr Trp Asn Ser Gln
    50                  55                  60

Lys Asp Ile Leu Glu Arg Ala Arg Ala Val Asp Thr Tyr Cys Arg
65                  70                  75                  80

His Asn Tyr Gly Val Gly Glu Ser Phe Thr Val Gln Arg Arg
                85                  90

<210> SEQ ID NO 57
<211> LENGTH: 94
<212> TYPE: PRT
<213> ORGANISM: BOVINE

<400> SEQUENCE: 57

Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
            20                  25                  30

Asn Gly Glu Glu Tyr Val Arg Phe Asp Ser Asp Trp Asp Glu Phe Arg
        35                  40                  45

Ala Val Thr Glu Leu Gly Arg Pro Ser Ala Glu Tyr Trp Asn Ser Gln
    50                  55                  60

Lys Asp Phe Leu Glu Arg Arg Arg Ala Glu Val Asp Thr Val Cys Arg
65                  70                  75                  80

His Asn Tyr Gly Val Val Glu Ser Phe Thr Val Gln Arg Arg
                85                  90

<210> SEQ ID NO 58
<211> LENGTH: 94
<212> TYPE: PRT
<213> ORGANISM: BOVINE

<400> SEQUENCE: 58

```
Arg Glu Ile Gln Pro His Phe Leu Glu Tyr Ser Thr Ser Glu Cys His
 1               5                  10                  15

Phe Phe Asn Gly Thr Glu Arg Val Arg Leu Leu Asp Arg Tyr Phe His
                20                  25                  30

Asn Gly Glu Glu Phe Val Arg Phe Asp Ser Asp Trp Gly Glu Tyr Arg
            35                  40                  45

Ala Val Thr Glu Leu Gly Arg Pro Asp Ala Glu Tyr Trp Asn Ser Gln
        50                  55                  60

Lys Glu Ile Leu Glu Arg Ala Arg Ala Ala Val Asp Thr Tyr Cys Arg
 65                  70                  75                  80

His Asn Tyr Gly Val Val Glu Ser Phe Thr Val Gln Arg Arg
                85                  90
```

<210> SEQ ID NO 59
<211> LENGTH: 94
<212> TYPE: PRT
<213> ORGANISM: BOVINE

<400> SEQUENCE: 59

```
Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asp Arg Tyr Tyr Thr
                20                  25                  30

Asn Gly Glu Glu Thr Val Arg Phe Asp Ser Asp Trp Gly Glu Phe Arg
            35                  40                  45

Ala Val Thr Glu Leu Gly Arg Gln Asp Ala Glu Tyr Trp Asn Ser Gln
        50                  55                  60

Lys Asp Phe Leu Glu Glu Lys Arg Ala Glu Val Asp Arg Val Cys Arg
 65                  70                  75                  80

His Asn Tyr Gly Gly Met Glu Ser Phe Thr Val Gln Arg Arg
                85                  90
```

<210> SEQ ID NO 60
<211> LENGTH: 94
<212> TYPE: PRT
<213> ORGANISM: BOVINE

<400> SEQUENCE: 60

```
Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
                20                  25                  30

Asn Gly Glu Glu Phe Val Arg Phe Asp Ser Asp Trp Gly Glu Tyr Arg
            35                  40                  45

Ala Val Thr Glu Leu Gly Arg Ala Asp Ala Glu Tyr Trp Asn Ser Gln
        50                  55                  60

Lys Glu Ile Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                85                  90
```

<210> SEQ ID NO 61
<211> LENGTH: 94
<212> TYPE: PRT
<213> ORGANISM: BOVINE

<400> SEQUENCE: 61

```
Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
                20                  25                  30

Asn Gly Glu Glu Tyr Val Arg Phe Asp Ser Asp Trp Asp Glu Phe Arg
            35                  40                  45

Ala Val Thr Glu Leu Gly Arg Pro Ser Ala Glu Tyr Trp Asn Ser Gln
        50                  55                  60

Lys Asp Phe Leu Glu Arg Arg Ala Glu Val Asp Thr Val Cys Arg
 65                  70                  75                  80

His Asn Tyr Gly Val Val Glu Ser Phe Thr Val Gln Arg Arg
                85                  90
```

<210> SEQ ID NO 62
<211> LENGTH: 94
<212> TYPE: PRT
<213> ORGANISM: BOVINE

<400> SEQUENCE: 62

```
Arg Glu Ile Gln Pro His Phe Leu Glu Tyr Ser Thr Ser Glu Cys His
 1               5                  10                  15

Phe Phe Asn Gly Thr Glu Arg Val Arg Phe Leu Asp Arg Tyr Phe His
                20                  25                  30

Asn Gly Glu Glu Phe Leu Arg Phe Asp Ser Asp Trp Gly Glu Tyr Arg
            35                  40                  45

Ala Val Thr Glu Leu Gly Arg Pro Asp Ala Glu Tyr Trp Asn Ser Gln
        50                  55                  60

Lys Glu Ile Leu Glu Arg Ala Arg Ala Val Asp Thr Tyr Cys Arg
 65                  70                  75                  80

His Asn Tyr Gly Gly Val Glu Ser Phe Thr Val Gln Arg Arg
                85                  90
```

<210> SEQ ID NO 63
<211> LENGTH: 94
<212> TYPE: PRT
<213> ORGANISM: BOVINE

<400> SEQUENCE: 63

```
Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
                20                  25                  30

Asn Gly Glu Glu Thr Val Arg Phe Asp Ser Asp Trp Gly Glu Phe Arg
            35                  40                  45

Ala Val Thr Glu Leu Gly Arg Gln Asp Ala Glu Tyr Trp Asn Ser Gln
        50                  55                  60

Lys Asp Phe Leu Glu Glu Lys Arg Ala Glu Val Asp Arg Val Cys Arg
 65                  70                  75                  80

His Asn Tyr Gly Gly Met Glu Ser Phe Thr Val Gln Arg Arg
                85                  90
```

<210> SEQ ID NO 64
<211> LENGTH: 94
<212> TYPE: PRT
<213> ORGANISM: BOVINE

<400> SEQUENCE: 64

```
Arg Glu Ile Gln Pro His Phe Leu Glu Tyr Thr Lys Lys Glu Cys His
```

```
                1               5                   10                  15
        Phe Phe Asn Gly Thr Glu Arg Val Arg Phe Leu Asn Arg Tyr Phe His
                        20                  25                  30

Asn Gly Glu Glu Phe Val Arg Phe Gly Ser Asp Trp Gly Glu Tyr Arg
                    35                  40                  45

Ala Val Thr Glu Leu Gly Arg Pro Asp Ala Glu Tyr Trp Asn Ser Gln
                50                  55                  60

Lys Glu Ile Leu Glu Arg Ala Arg Ala Ala Val Asp Thr Tyr Cys Arg
         65                  70                  75                  80

His Asn Tyr Gly Val Gly Glu Ser Phe Thr Val Gln Arg Arg
                        85                  90

<210> SEQ ID NO 65
<211> LENGTH: 94
<212> TYPE: PRT
<213> ORGANISM: BOVINE

<400> SEQUENCE: 65

Arg Glu Ile Gln Pro His Phe Leu Glu Tyr Ser Lys Ser Glu Cys His
         1               5                   10                  15

Phe Phe Asn Gly Thr Glu Arg Val Arg Phe Leu Asp Arg Tyr Phe His
                        20                  25                  30

Asn Gly Glu Glu Tyr Val Arg Phe Asp Ser Asp Trp Gly Glu Tyr Arg
                    35                  40                  45

Ala Val Thr Glu Leu Gly Gln Arg Val Ala Glu Tyr Cys Asn Ser Gln
                50                  55                  60

Lys Asp Phe Leu Glu Arg Ala Arg Ala Ala Val Asp Thr Tyr Cys Arg
         65                  70                  75                  80

His Asn Tyr Gly Val Gly Glu Ser Phe Thr Val Gln Arg Arg
                        85                  90

<210> SEQ ID NO 66
<211> LENGTH: 94
<212> TYPE: PRT
<213> ORGANISM: BOVINE

<400> SEQUENCE: 66

Arg Glu Ile Gln Pro His Phe Leu Glu Tyr Ser Lys Ser Glu Cys His
         1               5                   10                  15

Phe Phe Asn Gly Thr Glu Arg Val Arg Phe Leu Glu Arg Ser Phe Tyr
                        20                  25                  30

Asn Gly Glu Glu Asn Val Arg Phe Asp Ser Asp Trp Gly Glu Tyr Arg
                    35                  40                  45

Ala Val Thr Glu Leu Gly Arg Pro Asp Ala Glu Tyr Trp Asn Ser Gln
                50                  55                  60

Lys Asp Asp Leu Glu Arg Arg Ala Glu Val Asp Arg Val Cys Arg
         65                  70                  75                  80

His Asn Tyr Gly Val Gly Glu Ser Phe Thr Val Gln Arg Arg
                        85                  90

<210> SEQ ID NO 67
<211> LENGTH: 94
<212> TYPE: PRT
<213> ORGANISM: BOVINE

<400> SEQUENCE: 67

Arg Glu Ile Gln Pro His Phe Leu Glu Tyr Ser Thr Ser Glu Cys His
         1               5                   10                  15
```

-continued

```
Phe Phe Asn Gly Thr Glu Arg Val Arg Phe Leu Asp Arg Tyr Phe His
             20                  25                  30

Asn Gly Glu Glu Phe Val Arg Phe Asp Ser Asp Trp Gly Glu Tyr Arg
         35                  40                  45

Ala Val Thr Glu Leu Gly Arg Pro Asp Ala Glu Tyr Trp Asn Ser Gln
     50                  55                  60

Lys Glu Ile Leu Glu Arg Ala Arg Ala Ala Val Asp Thr Tyr Cys Arg
 65                  70                  75                  80

His Asn Tyr Gly Val Val Glu Ser Phe Thr Val Gln Arg Arg
                 85                  90
```

<210> SEQ ID NO 68
<211> LENGTH: 94
<212> TYPE: PRT
<213> ORGANISM: BOVINE

<400> SEQUENCE: 68

```
Arg Glu Ile Gln Pro His Phe Leu Glu Tyr Cys Lys Arg Glu Cys His
 1               5                  10                  15

Phe Phe Asn Gly Thr Glu Arg Val Arg Phe Leu Asp Arg Tyr Phe His
             20                  25                  30

Asn Gly Glu Glu Phe Val Arg Phe Asp Ser Asp Trp Gly Glu Tyr Arg
         35                  40                  45

Ala Val Thr Glu Leu Gly Arg Pro Ala Ala Lys Gln Trp Asn Ser Gln
     50                  55                  60

Lys Asp Phe Leu Glu Glu Lys Arg Ala Ala Val Asp Thr Tyr Cys Arg
 65                  70                  75                  80

His Asn Tyr Gly Val Val Glu Ser Phe Thr Val Gln Arg Arg
                 85                  90
```

<210> SEQ ID NO 69
<211> LENGTH: 94
<212> TYPE: PRT
<213> ORGANISM: BOVINE

<400> SEQUENCE: 69

```
Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Glu Arg Ser Phe Tyr
             20                  25                  30

Asn Gly Glu Glu Asn Val Arg Phe Asp Ser Asp Trp Gly Glu Tyr Arg
         35                  40                  45

Ala Val Thr Glu Leu Gly Arg Arg Val Ala Glu Gln Leu Asn Ser Gln
     50                  55                  60

Lys Asp Phe Leu Glu Gln Lys Arg Ala Asn Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 70
<211> LENGTH: 94
<212> TYPE: PRT
<213> ORGANISM: BOVINE

<400> SEQUENCE: 70

```
Arg Glu Ile Gln Pro His Phe Leu Glu Tyr Thr Lys Lys Glu Cys His
 1               5                  10                  15
```

```
Phe Phe Asn Gly Thr Glu Arg Val Arg Phe Leu Asp Arg Tyr Phe His
            20                  25                  30

Asn Gly Glu Glu Phe Val Arg Phe Asp Ser Asp Trp Gly Glu Tyr Arg
            35                  40                  45

Ala Val Thr Glu Leu Gly Arg Pro Asp Ala Lys Tyr Arg Asn Ser Gln
        50                  55                  60

Lys Asp Phe Leu Glu Glu Lys Arg Ala Gln Val Asp Thr Tyr Cys Arg
 65                 70                  75                  80

His Asn Tyr Gly Val Gly Glu Ser Phe Thr Val Gln Arg Arg
                85                  90

<210> SEQ ID NO 71
<211> LENGTH: 94
<212> TYPE: PRT
<213> ORGANISM: BOVINE

<400> SEQUENCE: 71

Arg Glu Ile Gln Pro His Phe Leu Gln Tyr His Lys Gly Glu Cys His
 1               5                  10                  15

Phe Phe Asn Gly Thr Glu Arg Val Arg Leu Leu Asp Arg His Phe Tyr
            20                  25                  30

Asn Gly Glu Glu Tyr Val Arg Phe Asp Ser Asp Trp Asp Glu Phe Arg
            35                  40                  45

Ala Val Thr Glu Leu Gly Arg Pro Ser Ala Glu Tyr Trp Asn Ser Gln
        50                  55                  60

Lys Asp Phe Leu Glu Arg Arg Ala Glu Val Asp Thr Val Cys Arg
 65                 70                  75                  80

His Asn Tyr Gly Val Val Glu Ser Phe Thr Val Gln Arg Arg
                85                  90

<210> SEQ ID NO 72
<211> LENGTH: 94
<212> TYPE: PRT
<213> ORGANISM: BOVINE

<400> SEQUENCE: 72

Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asn Arg Tyr Phe His
            20                  25                  30

Asn Gly Glu Glu Phe Val Arg Phe Asp Ser Asp Trp Gly Glu Tyr Arg
            35                  40                  45

Ala Val Thr Glu Leu Gly Arg Pro Asp Ala Glu Tyr Trp Asn Ser Gln
        50                  55                  60

Lys Asp Ile Leu Glu Arg Ala Arg Ala Ala Val Asp Thr Tyr Cys Arg
 65                 70                  75                  80

His Asn Tyr Gly Val Gly Glu Ser Phe Thr Val Gln Arg Arg
                85                  90

<210> SEQ ID NO 73
<211> LENGTH: 94
<212> TYPE: PRT
<213> ORGANISM: BOVINE

<400> SEQUENCE: 73

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Phe His
```

20                  25                  30

Asn Gly Glu Glu Tyr Val Arg Phe Asp Ser Asp Trp Gly Glu Tyr Arg
             35                  40                  45

Ala Val Thr Glu Leu Gly Gln Arg Val Ala Glu Tyr Cys Asn Ser Gln
         50                  55                  60

Lys Asp Phe Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 74
<211> LENGTH: 94
<212> TYPE: PRT
<213> ORGANISM: BOVINE

<400> SEQUENCE: 74

Arg Glu Ile Gln Pro His Phe Leu Glu Tyr Ser Lys Ser Glu Cys His
  1               5                  10                  15

Phe Phe Asn Gly Thr Glu Arg Val Arg Phe Leu Asp Arg Tyr Phe His
                 20                  25                  30

Asn Gly Glu Glu Tyr Val Arg Phe Asp Ser Asp Trp Gly Glu Tyr Arg
             35                  40                  45

Ala Val Thr Glu Leu Gly Gln Arg Val Ala Glu Tyr Ser Asn Ser Gln
         50                  55                  60

Lys Asp Phe Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 75
<211> LENGTH: 94
<212> TYPE: PRT
<213> ORGANISM: BOVINE

<400> SEQUENCE: 75

Arg Glu Ile Gln Pro His Phe Leu Glu Tyr Ser Lys Ser Glu Cys His
  1               5                  10                  15

Phe Phe Asn Gly Thr Glu Arg Val Arg Phe Leu Asp Arg Tyr Phe His
                 20                  25                  30

Asn Gly Glu Glu Tyr Val Arg Phe Asp Ser Asp Trp Gly Glu Tyr Arg
             35                  40                  45

Ala Val Thr Glu Leu Gly Gln Arg Val Ala Glu Tyr Cys Asn Ser Gln
         50                  55                  60

Lys Asp Phe Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 76
<211> LENGTH: 94
<212> TYPE: PRT
<213> ORGANISM: BOVINE

<400> SEQUENCE: 76

Arg Glu Ile Gln Pro His Phe Leu Glu Tyr Ser Lys Ser Glu Cys His
  1               5                  10                  15

Phe Phe Asn Gly Thr Glu Arg Val Arg Phe Leu Asp Arg Tyr Phe His
                 20                  25                  30

Asn Gly Glu Glu Tyr Val Arg Phe Asp Ser Asp Trp Gly Glu Tyr Arg
          35                  40                  45

Ala Val Thr Glu Leu Gly Gln Arg Val Ala Glu Tyr Cys Asn Ser Gln
     50                  55                  60

Lys Asp Phe Leu Glu Arg Ala Arg Ala Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 77
<211> LENGTH: 94
<212> TYPE: PRT
<213> ORGANISM: BOVINE

<400> SEQUENCE: 77

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Asn Val Arg Phe Asp Ser Asp Trp Gly Glu Phe Arg
          35                  40                  45

Ala Val Thr Glu Leu Gly Arg Pro Asp Ala Glu Gln Trp Asn Ser Gln
     50                  55                  60

Lys Asp Phe Leu Glu Ser Arg Thr Ala Val Asp Thr Tyr Cys Arg
 65                  70                  75                  80

His Asn Tyr Gly Val Phe Glu Ser Phe Thr Val Gln Arg Arg
                 85                  90

<210> SEQ ID NO 78
<211> LENGTH: 94
<212> TYPE: PRT
<213> ORGANISM: BOVINE

<400> SEQUENCE: 78

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Glu Arg Ser Phe Tyr
                 20                  25                  30

Asn Gly Glu Glu Asn Val Arg Phe Asp Ser Asp Trp Gly Glu Tyr Arg
          35                  40                  45

Ala Val Thr Glu Leu Gly Arg Pro Asp Ala Glu Tyr Trp Asn Ser Gln
     50                  55                  60

Lys Glu Ile Leu Glu Arg Arg Ala Glu Val Asp Arg Val Cys Arg
 65                  70                  75                  80

His Asn Tyr Gly Val Gly Glu Ser Phe Thr Val Gln Arg Arg
                 85                  90

<210> SEQ ID NO 79
<211> LENGTH: 94
<212> TYPE: PRT
<213> ORGANISM: BOVINE

<400> SEQUENCE: 79

Arg Glu Ile Gln Pro His Phe Leu Glu Tyr Ser Thr Ser Glu Cys His
 1               5                  10                  15

Phe Phe Asn Gly Thr Glu Arg Val Arg Tyr Leu Asp Arg Tyr Phe His
                 20                  25                  30

-continued

Asn Gly Glu Glu Phe Val Arg Phe Asp Ser Asp Trp Gly Glu Tyr Arg
             35                  40                  45

Ala Val Thr Glu Leu Gly Arg Arg Val Ala Glu Gln Leu Asn Gly Gln
 50                  55                  60

Lys Asp Thr Leu Glu Arg Glu Arg Ala Tyr Val Asp Tyr Tyr Cys Arg
 65                  70                  75                  80

His Asn Tyr Gly Val Val Glu Ser Phe Thr Val Gln Arg Arg
                 85                  90

<210> SEQ ID NO 80
<211> LENGTH: 94
<212> TYPE: PRT
<213> ORGANISM: BOVINE

<400> SEQUENCE: 80

Arg Glu Ile Gln Pro His Phe Leu Glu Tyr Ser Thr Ser Glu Cys His
 1               5                  10                  15

Phe Phe Asn Gly Thr Glu Arg Val Arg Tyr Leu Asp Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Arg Val Ala Glu Gln Leu Asn Gly Gln
 50                  55                  60

Lys Asp Thr Leu Glu Arg Glu Arg Ala Tyr Val Asp Tyr Tyr Cys Arg
 65                  70                  75                  80

His Asn Tyr Gly Val Val Glu Ser Phe Thr Val Gln Arg Arg
                 85                  90

<210> SEQ ID NO 81
<211> LENGTH: 94
<212> TYPE: PRT
<213> ORGANISM: BOVINE

<400> SEQUENCE: 81

Arg Glu Ile Gln Pro His Phe Leu Gln Tyr His Lys Gly Glu Cys His
 1               5                  10                  15

Phe Leu Asn Gly Thr Glu Arg Val Arg Leu Leu Asp Arg His Phe His
                 20                  25                  30

Asn Gly Glu Glu Tyr Val Arg Phe Asp Ser Asp Trp Asp Glu Phe Arg
             35                  40                  45

Ala Val Thr Glu Leu Gly Arg Pro Ser Ala Glu Tyr Trp Asn Ser Gln
 50                  55                  60

Lys Asp Phe Leu Glu Arg Arg Ala Glu Val Asp Thr Val Cys Arg
 65                  70                  75                  80

His Asn Tyr Gly Val Val Glu Ser Phe Thr Val Gln Arg Arg
                 85                  90

<210> SEQ ID NO 82
<211> LENGTH: 94
<212> TYPE: PRT
<213> ORGANISM: BOVINE

<400> SEQUENCE: 82

Arg Glu Ile Gln Pro His Phe Leu Glu Tyr His Lys Gly Glu Cys His
 1               5                  10                  15

Phe Phe Asn Gly Thr Glu Arg Val Arg Leu Leu Asp Arg Tyr Phe Tyr
                 20                  25                  30

Asn Gly Glu Glu Tyr Val Arg Phe Asp Ser Asp Trp Asp Glu Phe Arg

```
                35                  40                  45
Ala Val Thr Glu Leu Gly Arg Pro Ser Ala Glu Tyr Trp Asn Ser Gln
     50                  55                  60

Lys Asp Phe Leu Glu Arg Arg Ala Glu Val Asp Thr Val Cys Arg
 65                  70                  75                  80

His Asn Tyr Gly Val Gly Glu Ser Phe Thr Val Gln Arg Arg
                 85                  90

<210> SEQ ID NO 83
<211> LENGTH: 94
<212> TYPE: PRT
<213> ORGANISM: BOVINE

<400> SEQUENCE: 83

Arg Glu Ile Gln Pro His Phe Leu Glu Tyr His Lys Ser Glu Cys Arg
 1               5                  10                  15

Phe Phe His Gly Thr Glu Arg Val Arg Tyr Leu Asp Arg Tyr Phe Tyr
                 20                  25                  30

Asn Gly Glu Glu Tyr Val Arg Phe Asp Asn Asp Trp Gly Glu Phe Arg
             35                  40                  45

Ala Val Ala Glu Leu Gly Arg Pro Asp Ala Glu Tyr Trp Asn Ser Gln
     50                  55                  60

Lys Asp Phe Leu Glu Arg Lys Arg Ala Glu Val Asp Thr Tyr Cys Arg
 65                  70                  75                  80

His Asn Tyr Gly Val Ile Glu Ser Phe Thr Val Gln Arg Arg
                 85                  90

<210> SEQ ID NO 84
<211> LENGTH: 94
<212> TYPE: PRT
<213> ORGANISM: BOVINE

<400> SEQUENCE: 84

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Asn Val Arg Phe Asp Ser Asp Trp Gly Glu Phe Arg
             35                  40                  45

Ala Val Thr Glu Leu Gly Arg Pro Asp Ala Glu Gln Trp Asn Ser Gln
     50                  55                  60

Lys Asp Phe Leu Glu Ser Arg Arg Thr Ala Val Asp Thr Tyr Cys Arg
 65                  70                  75                  80

His Asn Tyr Gly Val Phe Glu Ser Phe Thr Val Gln Arg Arg
                 85                  90

<210> SEQ ID NO 85
<211> LENGTH: 94
<212> TYPE: PRT
<213> ORGANISM: BOVINE

<400> SEQUENCE: 85

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Phe Tyr
                 20                  25                  30

Asn Gly Glu Glu Tyr Val Arg Phe Asp Ser Asp Trp Gly Glu Phe Arg
             35                  40                  45
```

```
Ala Val Ala Glu Leu Gly Arg Pro Glu Ala Lys Tyr Trp Asn Ser Gln
 50                  55                  60

Lys Asp Ile Leu Glu Arg Lys Ala Val Asp Thr Tyr Cys Arg
 65                  70                  75                  80

His Asn Tyr Gly Val Ile Glu Ser Phe Thr Val Gln Arg Arg
                     85                  90
```

<210> SEQ ID NO 86
<211> LENGTH: 94
<212> TYPE: PRT
<213> ORGANISM: BOVINE

<400> SEQUENCE: 86

```
Arg Glu Ile Gln Pro His Phe Leu Glu Tyr Tyr Lys Lys Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Leu Thr Glu Leu Gly Arg Gln Asp Ala Glu Gln Trp Asn Ser Gln
 50                  55                  60

Lys Asp Ile Leu Glu Arg Ala Arg Ala Val Asp Thr Tyr Cys Arg
 65                  70                  75                  80

Tyr Asn Tyr Gly Val Gly Glu Ser Phe Thr Val Gln Arg Arg
                     85                  90
```

<210> SEQ ID NO 87
<211> LENGTH: 94
<212> TYPE: PRT
<213> ORGANISM: BOVINE

<400> SEQUENCE: 87

```
Arg Glu Ile Gln Pro His Phe Leu Glu Tyr Ser Thr Arg Glu Cys His
 1               5                  10                  15

Phe Phe Asn Gly Thr Glu Arg Val Arg Phe Leu Asp Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Pro Asp Ala Glu Tyr Trp His Ser Gln
 50                  55                  60

Lys Glu Ile Leu Glu Arg Ala Arg Ala Val Asp Thr Tyr Cys Arg
 65                  70                  75                  80

His Asn Tyr Gly Gly Val Glu Ser Phe Thr Val Gln Arg Arg
                     85                  90
```

<210> SEQ ID NO 88
<211> LENGTH: 94
<212> TYPE: PRT
<213> ORGANISM: BOVINE

<400> SEQUENCE: 88

```
Arg Glu Ile Gln Pro His Phe Leu Glu Tyr Tyr Lys Ser Glu Cys His
 1               5                  10                  15

Phe Phe Asn Gly Thr Glu Arg Val Arg Phe Leu Asp Arg Tyr Tyr Thr
                 20                  25                  30

Asn Gly Gly Glu Thr Val Arg Phe Asp Ser Asp Trp Gly Glu Phe Arg
             35                  40                  45
```

```
Ala Leu Thr Glu Leu Gly Arg Gln Asp Ala Gly Gln Trp Asn Ser Gln
        50                  55                  60

Lys Asp Phe Leu Glu Arg Ala Arg Ala Val Asp Thr Tyr Cys Arg
 65                  70                  75                  80

Tyr Asn Tyr Gly Val Gly Glu Ser Phe Thr Val Gln Arg Arg
                85                  90

<210> SEQ ID NO 89
<211> LENGTH: 94
<212> TYPE: PRT
<213> ORGANISM: BOVINE

<400> SEQUENCE: 89

Arg Glu Ile Gln Pro His Phe Leu Glu Tyr Thr Lys Lys Glu Cys His
 1               5                  10                  15

Phe Phe Asn Gly Thr Glu Arg Val Arg Leu Leu Glu Arg Tyr Phe Tyr
                20                  25                  30

Asn Gly Glu Glu Tyr Val Arg Phe Asp Ser Asp Trp Gly Glu Phe Arg
            35                  40                  45

Ala Val Ala Glu Leu Gly Arg Pro Asp Ala Lys Tyr Trp Asn Ser Gln
        50                  55                  60

Lys Asp Phe Leu Glu Ser Arg Arg Thr Ala Val Asp Thr Tyr Cys Arg
 65                  70                  75                  80

His Asn Tyr Gly Val Gly Glu Ser Phe Thr Val Gln Arg Arg
                85                  90

<210> SEQ ID NO 90
<211> LENGTH: 94
<212> TYPE: PRT
<213> ORGANISM: BOVINE

<400> SEQUENCE: 90

Arg Glu Ile Gln Pro His Phe Leu Glu Tyr Thr Lys Ser Glu Cys His
 1               5                  10                  15

Phe Phe Asn Gly Thr Glu Arg Val Arg Phe Leu Asp Arg Tyr Tyr Thr
                20                  25                  30

Asn Gly Glu Glu Asn Val Arg Phe Asp Ser Asp Trp Gly Glu Phe Arg
            35                  40                  45

Ala Val Thr Glu Leu Gly Arg Pro Asp Ala Glu Gln Trp Asn Ser Gln
        50                  55                  60

Lys Asp Phe Leu Glu Ser Arg Arg Thr Ala Val Asp Thr Tyr Cys Arg
 65                  70                  75                  80

His Asn Tyr Gly Val Phe Glu Ser Phe Thr Val Gln Arg Arg
                85                  90

<210> SEQ ID NO 91
<211> LENGTH: 94
<212> TYPE: PRT
<213> ORGANISM: BOVINE

<400> SEQUENCE: 91

Arg Glu Ile Gln Pro His Phe Leu Glu Tyr Ser Thr Ser Glu Cys His
 1               5                  10                  15

Phe Ser Asn Gly Thr Glu Arg Val Arg Leu Leu Asp Arg Tyr Phe His
                20                  25                  30

Asn Gly Glu Glu Phe Val Arg Phe Asp Ser Asp Trp Gly Glu Phe Arg
            35                  40                  45

Ala Val Ala Glu Leu Gly Arg Pro Asp Ala Glu Tyr Trp Asn Ser Gln
```

```
                 50                  55                  60
Lys Asp Phe Leu Glu Ser Arg Arg Thr Ala Val Asp Thr Tyr Cys Arg
 65                  70                  75                  80

His Asn Tyr Gly Val Ile Glu Ser Phe Thr Val Gln Arg Arg
                 85                  90

<210> SEQ ID NO 92
<211> LENGTH: 94
<212> TYPE: PRT
<213> ORGANISM: BOVINE

<400> SEQUENCE: 92

Arg Glu Ile Gln Pro His Phe Leu Glu Tyr Ser Thr Ser Glu Cys His
 1               5                  10                  15

Phe Phe Asn Gly Thr Glu Arg Val Arg Tyr Leu Asp Arg Tyr Phe His
                 20                  25                  30

Asn Gly Glu Glu Phe Val Arg Phe Asp Ser Asp Trp Gly Glu Tyr Arg
                 35                  40                  45

Ala Val Thr Glu Leu Gly Arg Arg Val Ala Glu Gln Leu Asn Gly Gln
             50                  55                  60

Lys Asp Thr Leu Glu Arg Glu Arg Ala Tyr Val Asp Thr Tyr Cys Arg
 65                  70                  75                  80

His Asn Tyr Gly Val Val Glu Ser Phe Thr Val Gln Arg Arg
                 85                  90

<210> SEQ ID NO 93
<211> LENGTH: 94
<212> TYPE: PRT
<213> ORGANISM: BOVINE

<400> SEQUENCE: 93

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Asn Val Arg Phe Asp Ser Asp Trp Gly Glu Phe Arg
                 35                  40                  45

Ala Val Thr Glu Leu Gly Arg Pro Glu Ala Lys Tyr Trp Asn Ser Gln
             50                  55                  60

Lys Glu Ile Leu Glu Arg Lys Arg Ala Ala Val Asp Thr Tyr Cys Arg
 65                  70                  75                  80

His Asn Tyr Gly Val Ile Glu Ser Phe Thr Val Gln Arg Arg
                 85                  90

<210> SEQ ID NO 94
<211> LENGTH: 94
<212> TYPE: PRT
<213> ORGANISM: BOVINE

<400> SEQUENCE: 94

Arg Glu Ile Gln Pro His Phe Leu Glu Tyr Tyr Lys Ser Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
                 35                  40                  45

Ala Leu Thr Glu Leu Gly Arg Gln Asp Ala Glu Gln Trp Asn Ser Gln
             50                  55                  60
```

```
Lys Asp Phe Leu Glu Arg Ala Arg Ala Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 95
<211> LENGTH: 94
<212> TYPE: PRT
<213> ORGANISM: BOVINE

<400> SEQUENCE: 95

```
Arg Glu Ile Gln Pro His Phe Leu Glu Tyr Tyr Lys Ser Glu Cys His
  1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Leu Thr Glu Leu Gly Arg Gln Asp Ala Glu Gln Trp Asn Ser Gln
         50                  55                  60

Lys Asp Phe Leu Glu Arg Ala Arg Ala Val Asp Thr Tyr Cys Arg
 65                  70                  75                  80

Tyr Asn Tyr Gly Val Gly Glu Ser Phe Thr Val Gln Arg Arg
                 85                  90
```

<210> SEQ ID NO 96
<211> LENGTH: 94
<212> TYPE: PRT
<213> ORGANISM: BOVINE

<400> SEQUENCE: 96

```
Arg Glu Ile Gln Pro His Phe Leu Glu Tyr Ser Thr Ser Glu Cys His
  1               5                  10                  15

Phe Phe Asn Gly Thr Glu Arg Val Arg Tyr Leu Asp Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Arg Val Ala Glu Gln Leu Asn Gly Gln
         50                  55                  60

Lys Asp Thr Leu Glu Arg Glu Arg Ala Tyr Val Asp Thr Tyr Cys Arg
 65                  70                  75                  80

His Asn Tyr Gly Val Val Glu Ser Phe Thr Val Gln Arg Arg
                 85                  90
```

<210> SEQ ID NO 97
<211> LENGTH: 94
<212> TYPE: PRT
<213> ORGANISM: BOVINE

<400> SEQUENCE: 97

```
Arg Glu Ile Gln Pro His Phe Leu Glu Tyr Ser Thr Ser Glu Cys His
  1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Val Thr Glu Leu Gly Arg Gln Asp Ala Glu Tyr Trp Asn Ser Gln
         50                  55                  60
```

```
Lys Asp Phe Leu Glu Glu Lys Arg Ala Ala Val Asp Thr Tyr Cys Arg
 65                  70                  75                  80

His Asn Tyr Gly Val Val Glu Ser Phe Thr Val Gln Arg Arg
                 85                  90
```

<210> SEQ ID NO 98
<211> LENGTH: 94
<212> TYPE: PRT
<213> ORGANISM: BOVINE

<400> SEQUENCE: 98

```
Arg Glu Ile Gln Pro His Phe Leu Glu Tyr Ser Thr Ser Glu Cys His
 1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Val Thr Glu Leu Gly Arg Gln Asp Ala Glu Tyr Trp Asn Ser Gln
         50                  55                  60

Lys Asp Phe Leu Glu Glu Lys Arg Ala Glu Val Asp Arg Val Cys Arg
 65                  70                  75                  80

His Asn Tyr Gly Val Gly Glu Ser Phe Thr Val Gln Arg Arg
                 85                  90
```

<210> SEQ ID NO 99
<211> LENGTH: 94
<212> TYPE: PRT
<213> ORGANISM: BOVINE

<400> SEQUENCE: 99

```
Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Glu Arg Ser Phe Tyr
                 20                  25                  30

Asn Gly Glu Glu Asn Val Arg Phe Asp Ser Asp Trp Gly Glu Tyr Arg
             35                  40                  45

Ala Val Thr Glu Leu Gly Arg Arg Val Ala Glu Gln Leu Asn Ser Gln
         50                  55                  60

Lys Asp Leu Leu Glu Ala Lys Arg Ala Asn Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 100
<211> LENGTH: 94
<212> TYPE: PRT
<213> ORGANISM: BOVINE

<400> SEQUENCE: 100

```
Arg Glu Ile Gln Pro His Phe Leu Glu Tyr Thr Lys Lys Glu Cys His
 1               5                  10                  15

Phe Phe Asn Gly Thr Glu Arg Val Arg Leu Leu Glu Arg Tyr Phe Tyr
                 20                  25                  30

Asn Gly Glu Glu Tyr Val Arg Phe Asp Ser Asp Trp Gly Glu Phe Arg
             35                  40                  45

Ala Val Ala Glu Leu Gly Arg Pro Asp Ala Lys Tyr Trp Asn Ser Gln
         50                  55                  60

Lys Asp Phe Leu Glu Ser Arg Arg Thr Ala Val Asp Thr Tyr Cys Arg
```

-continued

```
               65                  70                  75                  80
His Asn Tyr Gly Val Gly Glu Ser Phe Thr Val Gln Arg Arg
                85                  90
```

<210> SEQ ID NO 101
<211> LENGTH: 94
<212> TYPE: PRT
<213> ORGANISM: BOVINE

<400> SEQUENCE: 101

```
Arg Glu Ile Gln Pro His Phe Leu Glu Tyr Ser Lys Ser Glu Cys His
  1               5                  10                  15
Phe Phe Asn Gly Thr Glu Arg Val Arg Phe Leu Asp Arg Tyr Tyr Thr
                 20                  25                  30
Asn Gly Glu Glu Asn Val Arg Phe Asp Ser Asp Trp Gly Glu Phe Arg
             35                  40                  45
Ala Val Thr Glu Leu Gly Arg Pro Asp Ala Glu Gln Trp Asn Ser Gln
         50                  55                  60
Lys Asp Phe Leu Glu Ser Arg Arg Thr Ala Val Asp Thr Tyr Cys Arg
 65                  70                  75                  80
His Asn Tyr Gly Val Phe Glu Ser Phe Thr Val Gln Arg Arg
                 85                  90
```

<210> SEQ ID NO 102
<211> LENGTH: 94
<212> TYPE: PRT
<213> ORGANISM: BOVINE

<400> SEQUENCE: 102

```
Arg Glu Ile Gln Pro His Phe Leu Glu Tyr Thr Lys Lys Glu Cys His
  1               5                  10                  15
Phe Phe Asn Gly Thr Glu Arg Val Arg Phe Leu Asn Arg Tyr Phe His
                 20                  25                  30
Asn Gly Glu Glu Phe Val Arg Phe Asp Ser Asp Trp Gly Glu Tyr Arg
             35                  40                  45
Ala Val Thr Glu Leu Gly Arg Pro Asp Ala Glu Tyr Trp Asn Ser Gln
         50                  55                  60
Lys Glu Ile Leu Glu Arg Ala Arg Ala Ala Val Asp Thr Tyr Cys Arg
 65                  70                  75                  80
His Asn Tyr Gly Val Gly Glu Ser Phe Thr Val Gln Arg Arg
                 85                  90
```

<210> SEQ ID NO 103
<211> LENGTH: 94
<212> TYPE: PRT
<213> ORGANISM: BOVINE

<400> SEQUENCE: 103

```
Arg Glu Ile Gln Pro His Phe Leu Glu Tyr Ser Lys Ser Glu Cys His
  1               5                  10                  15
Phe Phe Asn Gly Thr Glu Arg Val Arg Phe Leu Asp Arg Tyr Phe His
                 20                  25                  30
Asn Gly Glu Glu Tyr Val Arg Phe Asp Ser Asp Trp Gly Glu Tyr Arg
             35                  40                  45
Ala Val Thr Glu Leu Gly Gln Arg Asp Ala Glu Tyr Cys Asn Ser Gln
         50                  55                  60
Lys Asp Phe Leu Glu Arg Ala Arg Ala Ala Val Asp Thr Tyr Cys Arg
 65                  70                  75                  80
```

```
His Asn Tyr Gly Val Gly Glu Ser Phe Thr Val Gln Arg Arg
                85                  90
```

<210> SEQ ID NO 104
<211> LENGTH: 94
<212> TYPE: PRT
<213> ORGANISM: BOVINE

<400> SEQUENCE: 104

```
Arg Glu Ile Gln Pro His Phe Leu Glu Tyr Thr Lys Lys Glu Cys His
 1               5                  10                  15

Phe Phe Asn Gly Thr Glu Arg Val Arg Phe Leu Asp Arg Tyr Phe His
                20                  25                  30

Asn Gly Glu Glu Phe Val Arg Phe Asp Ser Asp Trp Gly Glu Tyr Arg
            35                  40                  45

Ala Val Thr Glu Leu Gly Arg Pro Asp Ala Lys Tyr Trp Asn Ser Gln
        50                  55                  60

Lys Asp Phe Leu Glu Arg Ala Arg Ala Ala Val Asp Thr Tyr Cys Arg
 65                  70                  75                  80

His Asn Tyr Gly Val Gly Glu Ser Phe Thr Val Gln Arg Arg
                85                  90
```

<210> SEQ ID NO 105
<211> LENGTH: 94
<212> TYPE: PRT
<213> ORGANISM: BOVINE

<400> SEQUENCE: 105

```
Arg Glu Ile Gln Pro His Phe Leu Glu Tyr Ser Thr Ser Glu Cys His
 1               5                  10                  15

Phe Phe Asn Gly Thr Glu Arg Val Arg Tyr Leu Asp Arg Tyr Phe His
                20                  25                  30

Asn Gly Glu Glu Phe Val Arg Phe Asp Ser Asp Trp Gly Glu Tyr Arg
            35                  40                  45

Ala Val Thr Glu Leu Gly Arg Arg Val Ala Glu Gln Leu Asn Gly Gln
        50                  55                  60

Lys Asp Thr Leu Glu Arg Glu Arg Ala Tyr Val Asp Thr Tyr Cys Arg
 65                  70                  75                  80

His Asn Tyr Gly Val Val Glu Ser Phe Thr Val Gln Arg Arg
                85                  90
```

<210> SEQ ID NO 106
<211> LENGTH: 94
<212> TYPE: PRT
<213> ORGANISM: BOVINE

<400> SEQUENCE: 106

```
Arg Glu Ile Gln Pro His Phe Leu Glu Tyr His Lys Ser Glu Cys His
 1               5                  10                  15

Phe Phe Asn Gly Thr Glu Arg Val Arg Phe Leu Asp Arg Tyr Phe Tyr
                20                  25                  30

Asn Gly Glu Glu Tyr Val Arg Phe Asp Ser Asp Trp Gly Glu Phe Arg
            35                  40                  45

Ala Val Ala Glu Leu Gly Arg Pro Glu Ala Lys Tyr Trp Asn Ser Gln
        50                  55                  60

Lys Glu Ile Leu Glu Arg Lys Arg Ala Val Asp Thr Tyr Cys Arg
 65                  70                  75                  80
```

His Asn Tyr Gly Val Ile Glu Ser Phe Thr Val Gln Arg Arg
            85                  90

<210> SEQ ID NO 107
<211> LENGTH: 94
<212> TYPE: PRT
<213> ORGANISM: BOVINE

<400> SEQUENCE: 107

Arg Glu Ile Gln Pro His Phe Leu Glu Tyr Tyr Lys Ser Glu Cys His
  1               5                  10                  15

Phe Phe Asn Gly Thr Glu Arg Val Arg Phe Leu Asp Arg Tyr Tyr Thr
                 20                  25                  30

Asn Gly Glu Glu Thr Val Arg Phe Asp Ser Asp Trp Gly Glu Phe Arg
             35                  40                  45

Ala Leu Thr Glu Leu Gly Arg Gln Asp Ala Glu Gln Trp Asn Ser Gln
         50                  55                  60

Lys Asp Phe Leu Glu Arg Ala Arg Ala Ala Val Asp Thr Tyr Cys Arg
 65                  70                  75                  80

Tyr Asn Tyr Gly Val Gly Glu Ser Phe Thr Val Gln Arg Arg
            85                  90

<210> SEQ ID NO 108
<211> LENGTH: 94
<212> TYPE: PRT
<213> ORGANISM: BOVINE

<400> SEQUENCE: 108

Arg Glu Ile Gln Pro His Phe Leu Glu Tyr Ser Thr Ser Glu Cys His
  1               5                  10                  15

Phe Phe Asn Gly Thr Glu Arg Val Arg Phe Leu Asp Arg Tyr Phe His
                 20                  25                  30

Asn Gly Glu Glu Phe Val Arg Phe Asp Ser Asp Trp Gly Glu Tyr Arg
             35                  40                  45

Ala Val Thr Glu Leu Gly Arg Pro Asp Ala Glu Tyr Trp Asn Ser Gln
         50                  55                  60

Lys Glu Ile Leu Glu Arg Ala Arg Ala Ala Val Asp Thr Tyr Cys Arg
 65                  70                  75                  80

His Asn Tyr Gly Gly Val Glu Ser Phe Thr Val Gln Arg Arg
            85                  90

<210> SEQ ID NO 109
<211> LENGTH: 94
<212> TYPE: PRT
<213> ORGANISM: BOVINE

<400> SEQUENCE: 109

Arg Glu Ile Gln Pro His Phe Leu Glu Tyr Ser Thr Ser Glu Cys His
  1               5                  10                  15

Phe Ser Asn Gly Thr Glu Arg Val Arg Leu Leu Asp Arg Tyr Phe His
                 20                  25                  30

Asn Gly Glu Glu Phe Val Arg Phe Asp Ser Asp Trp Gly Glu Phe Arg
             35                  40                  45

Ala Val Ala Glu Leu Gly Arg Pro Asp Ala Glu Tyr Trp Asn Ser Gln
         50                  55                  60

Lys Asp Phe Leu Glu Ser Arg Arg Thr Ala Val Asp Thr Tyr Cys Arg
 65                  70                  75                  80

His Asn Tyr Gly Val Ile Glu Ser Phe Thr Val Gln Arg Arg 85                  90

<210> SEQ ID NO 110
<211> LENGTH: 94
<212> TYPE: PRT
<213> ORGANISM: BOVINE

<400> SEQUENCE: 110

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Phe His
             20                  25                  30

Asn Gly Glu Glu Tyr Val Arg Phe Asp Ser Asp Trp Gly Gly Tyr Arg
         35                  40                  45

Ala Val Thr Glu Leu Gly Gln Arg Val Ala Glu Tyr Cys Asn Ser Gln
     50                  55                  60

Lys Asp Phe Leu Glu Arg Ala Arg Ala Val Asp Thr Tyr Cys Arg
 65                  70                  75                  80

His Asn Tyr Gly Val Gly Glu Ser Phe Thr Val Gln Arg Arg
             85                  90

<210> SEQ ID NO 111
<211> LENGTH: 94
<212> TYPE: PRT
<213> ORGANISM: BOVINE

<400> SEQUENCE: 111

Arg Glu Ile Gln Pro His Phe Leu Glu Tyr Ser Lys Ser Glu Cys His
 1               5                  10                  15

Phe Phe Asn Gly Thr Glu Arg Val Arg Phe Leu Asp Arg Tyr Phe His
             20                  25                  30

Asn Gly Glu Glu Tyr Val Arg Phe Asp Ser Asp Trp Asp Glu Phe Arg
         35                  40                  45

Ala Val Thr Glu Leu Gly Arg Pro Ser Ala Glu Tyr Trp Asn Ser Gln
     50                  55                  60

Lys Asp Phe Leu Glu Arg Arg Arg Ala Glu Val Asp Thr Val Cys Arg
 65                  70                  75                  80

His Asn Tyr Gly Val Val Glu Ser Phe Thr Val Gln Arg Arg
             85                  90

<210> SEQ ID NO 112
<211> LENGTH: 4
<212> TYPE: PRT
<213> ORGANISM: BOVINE

<400> SEQUENCE: 112

Val Asp Thr Val
 1

<210> SEQ ID NO 113
<211> LENGTH: 4
<212> TYPE: PRT
<213> ORGANISM: BOVINE

<400> SEQUENCE: 113

Val Asp Arg Val
 1

<210> SEQ ID NO 114
<211> LENGTH: 18

-continued

```
<212> TYPE: DNA
<213> ORGANISM: Artificial Sequence
<220> FEATURE:
<223> OTHER INFORMATION: Description of Artificial Sequence: PRIMER

<400> SEQUENCE: 114
tgtaaaacga cggccagt                                                   18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 115
caggaaacag ctatgacc                                                   18
```